United States Patent
Nishida et al.

(10) Patent No.: US 10,920,215 B2
(45) Date of Patent: Feb. 16, 2021

(54) METHOD FOR MODIFYING GENOME SEQUENCE TO INTRODUCE SPECIFIC MUTATION TO TARGETED DNA SEQUENCE BY BASE-REMOVAL REACTION, AND MOLECULAR COMPLEX USED THEREIN

(71) Applicant: National University Corporation Kobe University, Kobe (JP)

(72) Inventors: Keiji Nishida, Kobe (JP); Akihiko Kondo, Kobe (JP)

(73) Assignee: National University Corporation Kobe University, Kobe (JP)

( * ) Notice: Subject to any disclaimer, the term of this patent is extended or adjusted under 35 U.S.C. 154(b) by 0 days.

(21) Appl. No.: 15/523,939

(22) PCT Filed: Nov. 2, 2015

(86) PCT No.: PCT/JP2015/080958
§ 371 (c)(1),
(2) Date: May 2, 2017

(87) PCT Pub. No.: WO2016/072399
PCT Pub. Date: May 12, 2016

(65) Prior Publication Data
US 2017/0321210 A1 Nov. 9, 2017

(30) Foreign Application Priority Data

Nov. 4, 2014 (JP) .................................. 2014-224745

(51) Int. Cl.
| | | |
|---|---|---|
| *C12N 15/10* | (2006.01) | |
| *C07K 19/00* | (2006.01) | |
| *C12N 9/24* | (2006.01) | |
| *C12N 15/09* | (2006.01) | |
| *C12N 9/22* | (2006.01) | |
| *C12N 15/11* | (2006.01) | |

(52) U.S. Cl.
CPC .......... *C12N 15/1024* (2013.01); *C07K 19/00* (2013.01); *C12N 9/22* (2013.01); *C12N 9/24* (2013.01); *C12N 9/2497* (2013.01); *C12N 15/09* (2013.01); *C12N 15/11* (2013.01); *C12Y 302/02027* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 6,117,680 A * | 9/2000 | Natesan | ............... | C07K 14/005 435/235.1 |
| 6,713,294 B1 * | 3/2004 | Krokan | ............... | C12Q 1/6848 435/18 |
| 9,840,699 B2 * | 12/2017 | Liu | .................. | C12Y 304/2206 |
| 2005/0208489 A1 | 9/2005 | Carroll et al. | | |
| 2006/0134631 A1 | 6/2006 | Krokan et al. | | |
| 2011/0002889 A1 | 1/2011 | Barrangou et al. | | |
| 2011/0145940 A1 | 6/2011 | Voytas et al. | | |
| 2014/0304853 A1 * | 10/2014 | Ainley | ............... | C12N 15/8213 800/278 |
| 2015/0037790 A1 * | 2/2015 | Fox | ........................ | C12Q 1/683 435/6.11 |
| 2017/0073670 A1 | 3/2017 | Nishida et al. | | |

FOREIGN PATENT DOCUMENTS

| | | | | |
|---|---|---|---|---|
| JP | 2010-519929 A | 6/2010 | | |
| JP | 4968498 B2 | 7/2012 | | |
| JP | 2013-513389 A | 4/2013 | | |
| JP | 2013-128413 A | 7/2013 | | |
| WO | WO 97/25416 A1 * | 7/1997 | ............... | C12N 9/24 |
| WO | WO 1997/025416 A2 | 7/1997 | | |
| WO | WO 2014/127287 A1 * | 8/2012 | ............ | C12N 15/90 |
| WO | WO 2014/074453 A1 | 5/2014 | | |
| WO | WO 2014/127287 A1 | 8/2014 | | |
| WO | WO 2015/133554 A1 | 9/2015 | | |

OTHER PUBLICATIONS

Jacobs et al. (2012) DNA glycosylases: in DNA repair and beyond. Chromosoma, 121:1-20 (Year: 2012).*
Chen et al. (2005) Mutations at Arginine 276 transform human uracil-DNA glycosylase into a single-stranded DNA-specific uracil-DNA glycosylase. DNA Repair, 4(7):793-805 (Year: 2005).*
Kavli et al. (1996) Excision of cytosine and thymine from DNA by mutants of human uracil-DNA glycosylase. The EMBO Journal, 15 (13):3442-3447 (Year: 1996).*
Wilstermann et al. (2001) Base Excision Repair Intermediates as Topoisomerase II Poisons. The Journal of Biological Chemistry, 276(49):46290-46296 (Year: 2001).*
Cong et al. (2013) Multiplex Genome Engineering Using CRISPR/Cas Systems. Science, 339:819-823 (Year: 2013).*
McNeill et al. (2007) A Dominant-Negative Form of the Major Human Abasic Endonuclease Enhances Cellular Sensitivity to Laboratory and Clinical DNA-Damaging Agents. Molecular Cancer Research, 5(1):61-70 (Year: 2007).*
Shekhawat et al. (2011) Split-protein systems: beyond binary protein-protein interactions. Current Opinion in Chemical Biology, 15: 789-797 (Year: 2011).*

(Continued)

*Primary Examiner* — Neil P Hammell
(74) *Attorney, Agent, or Firm* — Leydig, Voit & Mayer, Ltd.

(57) ABSTRACT

The present invention provides a method of modifying a targeted site of a double stranded DNA, including a step of contacting a complex wherein a nucleic acid sequence-recognizing module that specifically binds to a target nucleotide sequence in a selected double stranded DNA and DNA glycosylase with sufficiently low reactivity with a DNA having an unrelaxed double helix structure (unrelaxed DNA) are bonded, with the double stranded DNA, to convert one or more nucleotides in the targeted site to other one or more nucleotides or delete one or more nucleotides, or insert one or more nucleotides into the targeted site, without cleaving at least one strand of the double stranded DNA in the targeted site.

28 Claims, 11 Drawing Sheets

Specification includes a Sequence Listing.

(56) References Cited

OTHER PUBLICATIONS

P20536.1 (UniProt Reference sequence for vaccinia virus Uracil DNA glycosylase, priority to Oct. 16, 2013, 2 pages) (Year: 2013).*
Stanitsa et al. (2006) Vaccinia Virus Uracil DNA Glycosylase Interacts with the A20 Protein to Form a Heterodimeric Processivity Factor for the Viral DNA Polymerase. Journal of Biological Chemistry, 281(6):3439-3451 (Year: 2006).*
Chatterjee et al. (2001) Uracil-DNA glycosylase-deficient yeast exhibit a mitochondrial mutator phenotype. Nucleic Acids Research, 29(24):4935,4940 (Year: 2001).*
NP_003353.1 (Human UNG1 protein, NCBI Reference Sequence, priority to Sep. 12, 2013, 2 pages) (Year: 2013).*
NP_013691.1 (*Saccharomyces cerevisiae* UNG1 protein, NCBI Reference Sequence, priority to Sep. 6, 2013, 2 pages) (Year : 2013).*
Chen et al. (2005) Mutations at Arginine 276 transform human uracil-DNA glycosylase into a single-stranded DNA-specific uracil-DNA glycosylase. DNA Repair, 4:793-805 (Year: 2005).*
Chen et al., *DNA Repair*, 4(7): 793-805 (2005).
Esvelt et al., *Mol. Syst. Biol.*, 9: 641 (2013).
Finney-Manchester et al., *Nucleic Acids Res.*, 41(9): e99 (2013).
Kavli et al., *EMBO J.*, 15(13): 3442-3447 (1996).
Kwon et al., *Chem. Biol.*, 10: 351-359 (2003).
Nilsen et al., *EMBO J.*, 20(15): 4278-4826 (2001).
Slupphaug et al., *Nature*, 384(6604): 87-92 (1996).
Stanitsa et al., *J. Biol. Chem.*, 281(6): 3439-3451 (2006).
Wright et al., *Proc. Natl. Acad. Sci. U.S.A.*, 112(10): 2984-2989 (2015).
Zetsche et al., *Nat. Biotechnol.*, 33(2):139-142 (2015).
Japanese Patent Office, International Search Report in International Patent Application No. PCT/JP2015/080958 (dated Jan. 26, 2016).
Komor et al., "Programmable editing of a target base in genomic DNA without double-stranded DNA cleavage," *Nature*, 533(7603): 420-424 and supplemental on-line materials on methods and extended data (2016).
Ma et al., "Targeted Aid-mediated mutagenesis (TAM) enables efficient genomic diversification in mammalian cells," *Nat. Methods*, 13(12): 1029-1035 and supplemental on-line materials on methods (2016).
Nishida et al., "Targeted nucleotide editing using hybrid prokaryotic and vertebrate adaptive immune systems," *Science*, 353(6305): aaf8729 (Aug. 4, 2016).

* cited by examiner

SEQUENCE LISTING

```
<160> NUMBER OF SEQ ID NOS: 27

<210> SEQ ID NO 1
<211> LENGTH: 1077
<212> TYPE: DNA
<213> ORGANISM: Saccharomyces cerevisiae
<220> FEATURE:
<221> NAME/KEY: CDS
<222> LOCATION: (1)..(1077)
<220> FEATURE:
<221> NAME/KEY: transit_peptide
<222> LOCATION: (1)..(60)

<400> SEQUENCE: 1 atg tgg tgc atg aga aga ttg cca aca aat tca gtt atg acg gtg gct      48
Met Trp Cys Met Arg Arg Leu Pro Thr Asn Ser Val Met Thr Val Ala
1               5                   10                  15 cga aag aga aag caa act acg atc gaa gac ttc ttt ggt aca aag aaa      96
Arg Lys Arg Lys Gln Thr Thr Ile Glu Asp Phe Phe Gly Thr Lys Lys
                20                  25                  30 agc act aat gag gcg ccc aat aag aaa ggt aaa tcg ggc gct act ttc     144
Ser Thr Asn Glu Ala Pro Asn Lys Lys Gly Lys Ser Gly Ala Thr Phe
            35                  40                  45 atg acc ata aca aat ggc gca gct atc aag aca gag aca aag gcg gtc     192
Met Thr Ile Thr Asn Gly Ala Ala Ile Lys Thr Glu Thr Lys Ala Val
        50                  55                  60 gca aag gag gca aac acg gac aaa tat cct gct aat tca aat gca aaa     240
Ala Lys Glu Ala Asn Thr Asp Lys Tyr Pro Ala Asn Ser Asn Ala Lys
65                  70                  75                  80 gat gta tat tcg aag aac ttg agc agc aat tta cgt aca cta ctg tcg     288
Asp Val Tyr Ser Lys Asn Leu Ser Ser Asn Leu Arg Thr Leu Leu Ser
```

-continued

```
                85                  90                  95
ctg gag cta gaa acg att gat gat tcg tgg ttt cca cat tta atg gat      336
Leu Glu Leu Glu Thr Ile Asp Asp Ser Trp Phe Pro His Leu Met Asp
        100                 105                 110 gaa ttt aaa aag cca tat ttt gta aag ttg aaa cag ttt gtc act aaa      384
Glu Phe Lys Lys Pro Tyr Phe Val Lys Leu Lys Gln Phe Val Thr Lys
    115                 120                 125 gag caa gct gat cat aca gta ttt ccg cct gca aag gat att tac tca      432
Glu Gln Ala Asp His Thr Val Phe Pro Pro Ala Lys Asp Ile Tyr Ser
130                 135                 140 tgg acc agg cta acg cct ttt aat aaa gtt aaa gtc gtg att atc ggt      480
Trp Thr Arg Leu Thr Pro Phe Asn Lys Val Lys Val Val Ile Ile Gly
145                 150                 155                 160 caa gat ccc tac cac aac ttt aat cag gcg cat ggc ttg gct ttt agc      528
Gln Asp Pro Tyr His Asn Phe Asn Gln Ala His Gly Leu Ala Phe Ser
                165                 170                 175 gtc aaa ccc cct aca cca gca cca ccg tca tta aag aac ata tat aag      576
Val Lys Pro Pro Thr Pro Ala Pro Pro Ser Leu Lys Asn Ile Tyr Lys
        180                 185                 190 gaa ctg aag caa gag tat cct gat ttt gtt gaa gat aat aaa gtg gga      624
Glu Leu Lys Gln Glu Tyr Pro Asp Phe Val Glu Asp Asn Lys Val Gly
    195                 200                 205 gat tta act cac tgg gct tca caa ggg gtt tta ttg ctt aat acc tcg      672
Asp Leu Thr His Trp Ala Ser Gln Gly Val Leu Leu Leu Asn Thr Ser
210                 215                 220 tta act gta aga gca cat aat gca aac tcg cat tct aag cat ggt tgg      720
Leu Thr Val Arg Ala His Asn Ala Asn Ser His Ser Lys His Gly Trp
225                 230                 235                 240 gaa act ttt aca aaa agg gta gtt cag ttg ttg atc cag gac aga gag      768
Glu Thr Phe Thr Lys Arg Val Val Gln Leu Leu Ile Gln Asp Arg Glu
                245                 250                 255 gcc gac ggt aag agt tta gta ttc ctc tta tgg ggg aac aat gct atc      816
Ala Asp Gly Lys Ser Leu Val Phe Leu Leu Trp Gly Asn Asn Ala Ile
        260                 265                 270 aaa tta gta gag tct ctg ttg gga tct act tcc gtt gga agc ggt agt      864
Lys Leu Val Glu Ser Leu Leu Gly Ser Thr Ser Val Gly Ser Gly Ser
    275                 280                 285 aag tac cct aat atc atg gtg atg aag tca gtg cat ccg tct cca tta      912
Lys Tyr Pro Asn Ile Met Val Met Lys Ser Val His Pro Ser Pro Leu
290                 295                 300 agt gca agt aga gga ttt ttt ggt acc aac cat ttc aaa atg ata aac      960
Ser Ala Ser Arg Gly Phe Phe Gly Thr Asn His Phe Lys Met Ile Asn
305                 310                 315                 320 gat tgg cta tac aat acc cgc gga gag aaa atg ata gac tgg agt gtt      1008
Asp Trp Leu Tyr Asn Thr Arg Gly Glu Lys Met Ile Asp Trp Ser Val
                325                 330                 335 gtt cct gga acg tca tta aga gaa gtt cag gag gca aat gct cgc tta      1056
Val Pro Gly Thr Ser Leu Arg Glu Val Gln Glu Ala Asn Ala Arg Leu
        340                 345                 350 gag tca gaa tca aag gac cct                                          1077
Glu Ser Glu Ser Lys Asp Pro
    355
```

<210> SEQ ID NO 2
<211> LENGTH: 359
<212> TYPE: PRT
<213> ORGANISM: Saccharomyces cerevisiae

<400> SEQUENCE: 2

Met Trp Cys Met Arg Arg Leu Pro Thr Asn Ser Val Met Thr Val Ala

```
  1               5                  10                 15
Arg Lys Arg Lys Gln Thr Thr Ile Glu Asp Phe Phe Gly Thr Lys Lys
                 20                 25                 30

Ser Thr Asn Glu Ala Pro Asn Lys Lys Gly Lys Ser Gly Ala Thr Phe
             35                 40                 45

Met Thr Ile Thr Asn Gly Ala Ala Ile Lys Thr Glu Thr Lys Ala Val
        50                 55                 60

Ala Lys Glu Ala Asn Thr Asp Lys Tyr Pro Ala Asn Ser Asn Ala Lys
65                  70                 75                 80

Asp Val Tyr Ser Lys Asn Leu Ser Ser Asn Leu Arg Thr Leu Leu Ser
                85                 90                 95

Leu Glu Leu Glu Thr Ile Asp Asp Ser Trp Phe Pro His Leu Met Asp
                100                105                110

Glu Phe Lys Lys Pro Tyr Phe Val Lys Leu Lys Gln Phe Val Thr Lys
            115                120                125

Glu Gln Ala Asp His Thr Val Phe Pro Pro Ala Lys Asp Ile Tyr Ser
        130                135                140

Trp Thr Arg Leu Thr Pro Phe Asn Lys Val Lys Val Ile Ile Gly
145                 150                155                160

Gln Asp Pro Tyr His Asn Phe Asn Gln Ala His Gly Leu Ala Phe Ser
                165                170                175

Val Lys Pro Pro Thr Pro Ala Pro Pro Ser Leu Lys Asn Ile Tyr Lys
            180                185                190

Glu Leu Lys Gln Glu Tyr Pro Asp Phe Val Glu Asp Asn Lys Val Gly
            195                200                205

Asp Leu Thr His Trp Ala Ser Gln Gly Val Leu Leu Leu Asn Thr Ser
        210                215                220

Leu Thr Val Arg Ala His Asn Ala Asn Ser His Ser Lys His Gly Trp
225                 230                235                240

Glu Thr Phe Thr Lys Arg Val Val Gln Leu Leu Ile Gln Asp Arg Glu
                245                250                255

Ala Asp Gly Lys Ser Leu Val Phe Leu Leu Trp Gly Asn Asn Ala Ile
            260                265                270

Lys Leu Val Glu Ser Leu Leu Gly Ser Thr Ser Val Gly Ser Gly Ser
            275                280                285

Lys Tyr Pro Asn Ile Met Val Met Lys Ser Val His Pro Ser Pro Leu
            290                295                300

Ser Ala Ser Arg Gly Phe Phe Gly Thr Asn His Phe Lys Met Ile Asn
305                 310                315                320

Asp Trp Leu Tyr Asn Thr Arg Gly Glu Lys Met Ile Asp Trp Ser Val
                325                330                335

Val Pro Gly Thr Ser Leu Arg Glu Val Gln Glu Ala Asn Ala Arg Leu
            340                345                350

Glu Ser Glu Ser Lys Asp Pro
            355

<210> SEQ ID NO 3
<211> LENGTH: 4116
<212> TYPE: DNA
<213> ORGANISM: Artificial Sequence
<220> FEATURE:
<223> OTHER INFORMATION: Synthetic Streptococcus pyogenes-derived Cas9
      CDS optimized for eucaryotic expression
<220> FEATURE:
<221> NAME/KEY: CDS
<222> LOCATION: (1)..(4116)
```

-continued

<400> SEQUENCE: 3

```
atg gac aag aag tac tcc att ggg ctc gat atc ggc aca aac agc gtc        48
Met Asp Lys Lys Tyr Ser Ile Gly Leu Asp Ile Gly Thr Asn Ser Val
1               5                  10                  15 ggt tgg gcc gtc att acg gac gag tac aag gtg ccg agc aaa aaa ttc        96
Gly Trp Ala Val Ile Thr Asp Glu Tyr Lys Val Pro Ser Lys Lys Phe
            20                  25                  30 aaa gtt ctg ggc aat acc gat cgc cac agc ata aag aag aac ctc att       144
Lys Val Leu Gly Asn Thr Asp Arg His Ser Ile Lys Lys Asn Leu Ile
        35                  40                  45 ggc gcc ctc ctg ttc gac tcc ggg gag acg gcc gaa gcc acg cgg ctc       192
Gly Ala Leu Leu Phe Asp Ser Gly Glu Thr Ala Glu Ala Thr Arg Leu
    50                  55                  60 aaa aga aca gca cgg cgc aga tat acc cgc aga aag aat cgg atc tgc       240
Lys Arg Thr Ala Arg Arg Arg Tyr Thr Arg Arg Lys Asn Arg Ile Cys
65                  70                  75                  80 tac ctg cag gag atc ttt agt aat gag atg gct aag gtg gat gac tct       288
Tyr Leu Gln Glu Ile Phe Ser Asn Glu Met Ala Lys Val Asp Asp Ser
                85                  90                  95 ttc ttc cat agg ctg gag gag tcc ttt ttg gtg gag gag gat aaa aag       336
Phe Phe His Arg Leu Glu Glu Ser Phe Leu Val Glu Glu Asp Lys Lys
            100                 105                 110 cac gag cgc cac cca atc ttt ggc aat atc gtg gac gag gtg gcg tac       384
His Glu Arg His Pro Ile Phe Gly Asn Ile Val Asp Glu Val Ala Tyr
        115                 120                 125 cat gaa aag tac cca acc ata tat cat ctg agg aag aag ctt gta gac       432
His Glu Lys Tyr Pro Thr Ile Tyr His Leu Arg Lys Lys Leu Val Asp
    130                 135                 140 agt act gat aag gct gac ttg cgg ttg atc tat ctc gcg ctg gcg cat       480
Ser Thr Asp Lys Ala Asp Leu Arg Leu Ile Tyr Leu Ala Leu Ala His
145                 150                 155                 160 atg atc aaa ttt cgg gga cac ttc ctc atc gag ggg gac ctg aac cca       528
Met Ile Lys Phe Arg Gly His Phe Leu Ile Glu Gly Asp Leu Asn Pro
                165                 170                 175 gac aac agc gat gtc gac aaa ctc ttt atc caa ctg gtt cag act tac       576
Asp Asn Ser Asp Val Asp Lys Leu Phe Ile Gln Leu Val Gln Thr Tyr
            180                 185                 190 aat cag ctt ttc gaa gag aac ccg atc aac gca tcc gga gtt gac gcc       624
Asn Gln Leu Phe Glu Glu Asn Pro Ile Asn Ala Ser Gly Val Asp Ala
        195                 200                 205 aaa gca atc ctg agc gct agg ctg tcc aaa tcc cgg cgg ctc gaa aac       672
Lys Ala Ile Leu Ser Ala Arg Leu Ser Lys Ser Arg Arg Leu Glu Asn
    210                 215                 220 ctc atc gca cag ctc cct ggg gag aag aag aac ggc ctg ttt ggt aat       720
Leu Ile Ala Gln Leu Pro Gly Glu Lys Lys Asn Gly Leu Phe Gly Asn
225                 230                 235                 240 ctt atc gcc ctg tca ctc ggg ctg acc ccc aac ttt aaa tct aac ttc       768
Leu Ile Ala Leu Ser Leu Gly Leu Thr Pro Asn Phe Lys Ser Asn Phe
                245                 250                 255 gac ctg gcc gaa gat gcc aag ctt caa ctg agc aaa gac acc tac gat       816
Asp Leu Ala Glu Asp Ala Lys Leu Gln Leu Ser Lys Asp Thr Tyr Asp
            260                 265                 270 gat gat ctc gac aat ctg ctg gcc cag atc ggc gac cag tac gca gac       864
Asp Asp Leu Asp Asn Leu Leu Ala Gln Ile Gly Asp Gln Tyr Ala Asp
        275                 280                 285 ctt ttt ttg gcg gca aag aac ctg tca gac gcc att ctg ctg agt gat       912
Leu Phe Leu Ala Ala Lys Asn Leu Ser Asp Ala Ile Leu Leu Ser Asp
    290                 295                 300
```

```
att ctg cga gtg aac acg gag atc acc aaa gct ccg ctg agc gct agt      960
Ile Leu Arg Val Asn Thr Glu Ile Thr Lys Ala Pro Leu Ser Ala Ser
305                 310                 315                 320 atg atc aag cgc tat gat gag cac cac caa gac ttg act ttg ctg aag     1008
Met Ile Lys Arg Tyr Asp Glu His His Gln Asp Leu Thr Leu Leu Lys
                325                 330                 335 gcc ctt gtc aga cag caa ctg cct gag aag tac aag gaa att ttc ttc     1056
Ala Leu Val Arg Gln Gln Leu Pro Glu Lys Tyr Lys Glu Ile Phe Phe
            340                 345                 350 gat cag tct aaa aat ggc tac gcc gga tac att gac ggc gga gca agc     1104
Asp Gln Ser Lys Asn Gly Tyr Ala Gly Tyr Ile Asp Gly Gly Ala Ser
        355                 360                 365 cag gag gaa ttt tac aaa ttt att aag ccc atc ttg gaa aaa atg gac     1152
Gln Glu Glu Phe Tyr Lys Phe Ile Lys Pro Ile Leu Glu Lys Met Asp
    370                 375                 380 ggc acc gag gag ctg ctg gta aag ctt aac aga gaa gat ctg ttg cgc     1200
Gly Thr Glu Glu Leu Leu Val Lys Leu Asn Arg Glu Asp Leu Leu Arg
385                 390                 395                 400 aaa cag cgc act ttc gac aat gga agc atc ccc cac cag att cac ctg     1248
Lys Gln Arg Thr Phe Asp Asn Gly Ser Ile Pro His Gln Ile His Leu
                405                 410                 415 ggc gaa ctg cac gct atc ctc agg cgg caa gag gat ttc tac ccc ttt     1296
Gly Glu Leu His Ala Ile Leu Arg Arg Gln Glu Asp Phe Tyr Pro Phe
            420                 425                 430 ttg aaa gat aac agg gaa aag att gag aaa atc ctc aca ttt cgg ata     1344
Leu Lys Asp Asn Arg Glu Lys Ile Glu Lys Ile Leu Thr Phe Arg Ile
        435                 440                 445 ccc tac tat gta ggc ccc ctc gcc cgg gga aat tcc aga ttc gcg tgg     1392
Pro Tyr Tyr Val Gly Pro Leu Ala Arg Gly Asn Ser Arg Phe Ala Trp
    450                 455                 460 atg act cgc aaa tca gaa gag acc atc act ccc tgg aac ttc gag gaa     1440
Met Thr Arg Lys Ser Glu Glu Thr Ile Thr Pro Trp Asn Phe Glu Glu
465                 470                 475                 480 gtc gtg gat aag ggg gcc tct gcc cag tcc ttc atc gaa agg atg act     1488
Val Val Asp Lys Gly Ala Ser Ala Gln Ser Phe Ile Glu Arg Met Thr
                485                 490                 495 aac ttt gat aaa aat ctg cct aac gaa aag gtg ctt cct aaa cac tct     1536
Asn Phe Asp Lys Asn Leu Pro Asn Glu Lys Val Leu Pro Lys His Ser
            500                 505                 510 ctg ctg tac gag tac ttc aca gtt tat aac gag ctc acc aag gtc aaa     1584
Leu Leu Tyr Glu Tyr Phe Thr Val Tyr Asn Glu Leu Thr Lys Val Lys
        515                 520                 525 tac gtc aca gaa ggg atg aga aag cca gca ttc ctg tct gga gag cag     1632
Tyr Val Thr Glu Gly Met Arg Lys Pro Ala Phe Leu Ser Gly Glu Gln
    530                 535                 540 aag aaa gct atc gtg gac ctc ctc ttc aag acg aac cgg aaa gtt acc     1680
Lys Lys Ala Ile Val Asp Leu Leu Phe Lys Thr Asn Arg Lys Val Thr
545                 550                 555                 560 gtg aaa cag ctc aaa gaa gac tat ttc aaa aag att gaa tgt ttc gac     1728
Val Lys Gln Leu Lys Glu Asp Tyr Phe Lys Lys Ile Glu Cys Phe Asp
                565                 570                 575 tct gtt gaa atc agc gga gtg gag gat cgc ttc aac gca tcc ctg gga     1776
Ser Val Glu Ile Ser Gly Val Glu Asp Arg Phe Asn Ala Ser Leu Gly
            580                 585                 590 acg tat cac gat ctc ctg aaa atc att aaa gac aag gac ttc ctg gac     1824
Thr Tyr His Asp Leu Leu Lys Ile Ile Lys Asp Lys Asp Phe Leu Asp
        595                 600                 605 aat gag gag aac gag gac att ctt gag gac att gtc ctc acc ctt acg     1872
Asn Glu Glu Asn Glu Asp Ile Leu Glu Asp Ile Val Leu Thr Leu Thr
    610                 615                 620
```

```
ttg ttt gaa gat agg gag atg att gaa gaa cgc ttg aaa act tac gct    1920
Leu Phe Glu Asp Arg Glu Met Ile Glu Glu Arg Leu Lys Thr Tyr Ala
625                 630                 635                 640 cat ctc ttc gac gac aaa gtc atg aaa cag ctc aag agg cgc cga tat    1968
His Leu Phe Asp Asp Lys Val Met Lys Gln Leu Lys Arg Arg Arg Tyr
            645                 650                 655 aca gga tgg ggg cgg ctg tca aga aaa ctg atc aat ggg atc cga gac    2016
Thr Gly Trp Gly Arg Leu Ser Arg Lys Leu Ile Asn Gly Ile Arg Asp
        660                 665                 670 aag cag agt gga aag aca atc ctg gat ttt ctt aag tcc gat gga ttt    2064
Lys Gln Ser Gly Lys Thr Ile Leu Asp Phe Leu Lys Ser Asp Gly Phe
    675                 680                 685 gcc aac cgg aac ttc atg cag ttg atc cat gat gac tct ctc acc ttt    2112
Ala Asn Arg Asn Phe Met Gln Leu Ile His Asp Asp Ser Leu Thr Phe
690                 695                 700 aag gag gac atc cag aaa gca caa gtt tct ggc cag ggg gac agt ctt    2160
Lys Glu Asp Ile Gln Lys Ala Gln Val Ser Gly Gln Gly Asp Ser Leu
705                 710                 715                 720 cac gag cac atc gct aat ctt gca ggt agc cca gct atc aaa aag gga    2208
His Glu His Ile Ala Asn Leu Ala Gly Ser Pro Ala Ile Lys Lys Gly
            725                 730                 735 ata ctg cag acc gtt aag gtc gtg gat gaa ctc gtc aaa gta atg gga    2256
Ile Leu Gln Thr Val Lys Val Val Asp Glu Leu Val Lys Val Met Gly
        740                 745                 750 agg cat aag ccc gag aat atc gtt atc gag atg gcc cga gag aac caa    2304
Arg His Lys Pro Glu Asn Ile Val Ile Glu Met Ala Arg Glu Asn Gln
    755                 760                 765 act acc cag aag gga cag aag aac agt agg gaa agg atg aag agg att    2352
Thr Thr Gln Lys Gly Gln Lys Asn Ser Arg Glu Arg Met Lys Arg Ile
770                 775                 780 gaa gag ggt ata aaa gaa ctg ggg tcc caa atc ctt aag gaa cac cca    2400
Glu Glu Gly Ile Lys Glu Leu Gly Ser Gln Ile Leu Lys Glu His Pro
785                 790                 795                 800 gtt gaa aac acc cag ctt cag aat gag aag ctc tac ctg tac tac ctg    2448
Val Glu Asn Thr Gln Leu Gln Asn Glu Lys Leu Tyr Leu Tyr Tyr Leu
            805                 810                 815 cag aac ggc agg gac atg tac gtg gat cag gaa ctg gac atc aat cgg    2496
Gln Asn Gly Arg Asp Met Tyr Val Asp Gln Glu Leu Asp Ile Asn Arg
        820                 825                 830 ctc tcc gac tac gac gtg gat cat atc gtg ccc cag tct ttt ctc aaa    2544
Leu Ser Asp Tyr Asp Val Asp His Ile Val Pro Gln Ser Phe Leu Lys
    835                 840                 845 gat gat tct att gat aat aaa gtg ttg aca aga tcc gat aaa aat aga    2592
Asp Asp Ser Ile Asp Asn Lys Val Leu Thr Arg Ser Asp Lys Asn Arg
850                 855                 860 ggg aag agt gat aac gtc ccc tca gaa gaa gtt gtc aag aaa atg aaa    2640
Gly Lys Ser Asp Asn Val Pro Ser Glu Glu Val Val Lys Lys Met Lys
865                 870                 875                 880 aat tat tgg cgg cag ctg ctg aac gcc aaa ctg atc aca caa cgg aag    2688
Asn Tyr Trp Arg Gln Leu Leu Asn Ala Lys Leu Ile Thr Gln Arg Lys
            885                 890                 895 ttc gat aat ctg act aag gct gaa cga ggt ggc ctg tct gag ttg gat    2736
Phe Asp Asn Leu Thr Lys Ala Glu Arg Gly Gly Leu Ser Glu Leu Asp
        900                 905                 910 aaa gcc ggc ttc atc aaa agg cag ctt gtt gag aca cgc cag atc acc    2784
Lys Ala Gly Phe Ile Lys Arg Gln Leu Val Glu Thr Arg Gln Ile Thr
    915                 920                 925 aag cac gtg gcc caa att ctc gat tca cgc atg aac acc aag tac gat    2832
Lys His Val Ala Gln Ile Leu Asp Ser Arg Met Asn Thr Lys Tyr Asp
```

```
                       930                 935                  940
gaa aat gac aaa ctg att cga gag gtg aaa gtt att act ctg aag tct    2880
Glu Asn Asp Lys Leu Ile Arg Glu Val Lys Val Ile Thr Leu Lys Ser
945                 950                  955                  960 aag ctg gtc tca gat ttc aga aag gac ttt cag ttt tat aag gtg aga    2928
Lys Leu Val Ser Asp Phe Arg Lys Asp Phe Gln Phe Tyr Lys Val Arg
                965                  970                  975 gag atc aac aat tac cac cat gcg cat gat gcc tac ctg aat gca gtg    2976
Glu Ile Asn Asn Tyr His His Ala His Asp Ala Tyr Leu Asn Ala Val
                980                  985                  990 gta ggc act gca ctt atc aaa aaa tat ccc aag ctt gaa tct gaa ttt    3024
Val Gly Thr Ala Leu Ile Lys Lys Tyr Pro Lys Leu Glu Ser Glu Phe
                995                  1000                 1005 gtt tac gga gac tat aaa gtg tac gat gtt agg aaa atg atc gca        3069
Val Tyr Gly Asp Tyr Lys Val Tyr Asp Val Arg Lys Met Ile Ala
    1010                 1015                 1020 aag tct gag cag gaa ata ggc aag gcc acc gct aag tac ttc ttt        3114
Lys Ser Glu Gln Glu Ile Gly Lys Ala Thr Ala Lys Tyr Phe Phe
    1025                 1030                 1035 tac agc aat att atg aat ttt ttc aag acc gag att aca ctg gcc        3159
Tyr Ser Asn Ile Met Asn Phe Phe Lys Thr Glu Ile Thr Leu Ala
    1040                 1045                 1050 aat gga gag att cgg aag cga cca ctt atc gaa aca aac gga gaa        3204
Asn Gly Glu Ile Arg Lys Arg Pro Leu Ile Glu Thr Asn Gly Glu
    1055                 1060                 1065 aca gga gaa atc gtg tgg gac aag ggt agg gat ttc gcg aca gtc        3249
Thr Gly Glu Ile Val Trp Asp Lys Gly Arg Asp Phe Ala Thr Val
    1070                 1075                 1080 cgg aag gtc ctg tcc atg ccg cag gtg aac atc gtt aaa aag acc        3294
Arg Lys Val Leu Ser Met Pro Gln Val Asn Ile Val Lys Lys Thr
    1085                 1090                 1095 gaa gta cag acc gga ggc ttc tcc aag gaa agt atc ctc ccg aaa        3339
Glu Val Gln Thr Gly Gly Phe Ser Lys Glu Ser Ile Leu Pro Lys
    1100                 1105                 1110 agg aac agc gac aag ctg atc gca cgc aaa aaa gat tgg gac ccc        3384
Arg Asn Ser Asp Lys Leu Ile Ala Arg Lys Lys Asp Trp Asp Pro
    1115                 1120                 1125 aag aaa tac ggc gga ttc gat tct cct aca gtc gct tac agt gta        3429
Lys Lys Tyr Gly Gly Phe Asp Ser Pro Thr Val Ala Tyr Ser Val
    1130                 1135                 1140 ctg gtt gtg gcc aaa gtg gag aaa ggg aag tct aaa aaa ctc aaa        3474
Leu Val Val Ala Lys Val Glu Lys Gly Lys Ser Lys Lys Leu Lys
    1145                 1150                 1155 agc gtc aag gaa ctg ctg ggc atc aca atc atg gag cga tca agc        3519
Ser Val Lys Glu Leu Leu Gly Ile Thr Ile Met Glu Arg Ser Ser
    1160                 1165                 1170 ttc gaa aaa aac ccc atc gac ttt ctc gag gcg aaa gga tat aaa        3564
Phe Glu Lys Asn Pro Ile Asp Phe Leu Glu Ala Lys Gly Tyr Lys
    1175                 1180                 1185 gag gtc aaa aaa gac ctc atc att aag ctt ccc aag tac tct ctc        3609
Glu Val Lys Lys Asp Leu Ile Ile Lys Leu Pro Lys Tyr Ser Leu
    1190                 1195                 1200 ttt gag ctt gaa aac ggc cgg aaa cga atg ctc gct agt gcg ggc        3654
Phe Glu Leu Glu Asn Gly Arg Lys Arg Met Leu Ala Ser Ala Gly
    1205                 1210                 1215 gag ctg cag aaa ggt aac gag ctg gca ctg ccc tct aaa tac gtt        3699
Glu Leu Gln Lys Gly Asn Glu Leu Ala Leu Pro Ser Lys Tyr Val
    1220                 1225                 1230 aat ttc ttg tat ctg gcc agc cac tat gaa aag ctc aaa ggg tct        3744
```

```
Asn Phe Leu Tyr Leu Ala Ser His Tyr Glu Lys Leu Lys Gly Ser
    1235                1240                1245 ccc gaa gat aat gag cag aag cag ctg ttc gtg gaa caa cac aaa         3789
Pro Glu Asp Asn Glu Gln Lys Gln Leu Phe Val Glu Gln His Lys
    1250                1255                1260 cac tac ctt gat gag atc atc gag caa ata agc gaa ttc tcc aaa         3834
His Tyr Leu Asp Glu Ile Ile Glu Gln Ile Ser Glu Phe Ser Lys
    1265                1270                1275 aga gtg atc ctc gcc gac gct aac ctc gat aag gtg ctt tct gct         3879
Arg Val Ile Leu Ala Asp Ala Asn Leu Asp Lys Val Leu Ser Ala
    1280                1285                1290 tac aat aag cac agg gat aag ccc atc agg gag cag gca gaa aac         3924
Tyr Asn Lys His Arg Asp Lys Pro Ile Arg Glu Gln Ala Glu Asn
    1295                1300                1305 att atc cac ttg ttt act ctg acc aac ttg ggc gcg cct gca gcc         3969
Ile Ile His Leu Phe Thr Leu Thr Asn Leu Gly Ala Pro Ala Ala
    1310                1315                1320 ttc aag tac ttc gac acc acc ata gac aga aag cgg tac acc tct         4014
Phe Lys Tyr Phe Asp Thr Thr Ile Asp Arg Lys Arg Tyr Thr Ser
    1325                1330                1335 aca aag gag gtc ctg gac gcc aca ctg att cat cag tca att acg         4059
Thr Lys Glu Val Leu Asp Ala Thr Leu Ile His Gln Ser Ile Thr
    1340                1345                1350 ggg ctc tat gaa aca aga atc gac ctc tct cag ctc ggt gga gac         4104
Gly Leu Tyr Glu Thr Arg Ile Asp Leu Ser Gln Leu Gly Gly Asp
    1355                1360                1365 agc agg gct gac                                                      4116
Ser Arg Ala Asp
    1370

<210> SEQ ID NO 4
<211> LENGTH: 1372
<212> TYPE: PRT
<213> ORGANISM: Artificial Sequence
<220> FEATURE:
<223> OTHER INFORMATION: Synthetic Construct

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
        340                 345                 350

Asp Gln Ser Lys Asn Gly Tyr Ala Gly Tyr Ile Asp Gly Gly Ala Ser
    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
```

-continued

```
                580                 585                 590
Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
            995                 1000                1005
```

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Ser Arg Ala Asp
1370

<210> SEQ ID NO 5
<211> LENGTH: 83

```
<212> TYPE: DNA
<213> ORGANISM: Streptococcus pyogenes

<400> SEQUENCE: 5
gttttagagc tagaaatagc aagttaaaat aaggctagtc cgttatcaac ttgaaaaagt    60
ggcaccgagt cggtggtgct ttt                                           83

<210> SEQ ID NO 6
<211> LENGTH: 665
<212> TYPE: DNA
<213> ORGANISM: Saccharomyces cerevisiae

<400> SEQUENCE: 6
tttcaaaaat tcttactttt tttttggatg gacgcaaaga agtttaataa tcatattaca    60
tggcattacc accatataca tatccatata catatccata tctaatctta cttatatgtt   120
gtggaaatgt aaagagcccc attatcttag cctaaaaaaa ccttctcttt ggaactttca   180
gtaatacgct taactgctca ttgctatatt gaagtacgga ttagaagccg ccgagcgggt   240
gacagccctc cgaaggaaga ctctcctccg tgcgtcctcg tcttcaccgg tcgcgttcct   300
gaaacgcaga gtgtgcctcg ccgcactgc tccgaacaat aaagattcta caatactagc    360
ttttatggtt atgaagagga aaaattggca gtaacctggc cccacaaacc ttcaaatgaa   420
cgaatcaaat taacaaccat aggatgataa tgcgattagt tttttagcct tatttctggg   480
gtaattaatc agcgaagcga tgattttga tctattaaca gatatataaa tgcaaaaact   540
gcataaccac tttaactaat actttcaaca ttttcggttt gtattacttc ttattcaaat   600
gtaataaaag tatcaacaaa aaattgttaa tatacctcta tactttaacg tcaaggagaa   660
aaaac                                                              665

<210> SEQ ID NO 7
<211> LENGTH: 21
<212> TYPE: DNA
<213> ORGANISM: Artificial Sequence
<220> FEATURE:
<223> OTHER INFORMATION: Synthetic Nuclear transition signal
<220> FEATURE:
<221> NAME/KEY: CDS
<222> LOCATION: (1)..(21)

<400> SEQUENCE: 7 ccc aag aag aag agg aag gtg                                        21
Pro Lys Lys Lys Arg Lys Val
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Pro Lys Lys Lys Arg Lys Val
1               5

<210> SEQ ID NO 9
<211> LENGTH: 15
<212> TYPE: DNA
<213> ORGANISM: Artificial Sequence
<220> FEATURE:
<223> OTHER INFORMATION: Synthetic GS linker
<220> FEATURE:
```

-continued

```
<221> NAME/KEY: CDS
<222> LOCATION: (1)..(15)

<400> SEQUENCE: 9 ggt gga gga ggt tct                                              15
Gly Gly Gly Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Gly Gly Gly Gly Ser
1               5

<210> SEQ ID NO 11
<211> LENGTH: 188
<212> TYPE: DNA
<213> ORGANISM: Saccharomyces cerevisiae

<400> SEQUENCE: 11
gcgaatttct tatgatttat gatttttatt attaaataag ttataaaaaa aataagtgta    60
tacaaatttt aaagtgactc ttaggtttta aaacgaaaat tcttattctt gagtaactct   120
ttcctgtagg tcaggttgct ttctcaggta tagcatgagg tcgctcttat tgaccacacc   180
tctaccgg                                                           188

<210> SEQ ID NO 12
<211> LENGTH: 417
<212> TYPE: DNA
<213> ORGANISM: Saccharomyces cerevisiae

<400> SEQUENCE: 12
ataccaggca tggagcttat ctggtccgtt cgagttttcg acgagtttgg agacattctt    60
tatagatgtc ctttttttt aatgatattc gttaaagaac aaaaagtcaa agcagtttaa   120
cctaacacct gttgttgatg ctacttgaaa caaggcttct aggcgaatac ttaaaaaggt   180
aatttcaata gcggtttata tatctgtttg cttttcaaga tattatgtaa acgcacgatg   240
tttttcgccc aggctttatt ttttttgttg ttgttgtctt ctcgaagaat tttctcgggc   300
agatctttgt cggaatgtaa aaaagcgcgt aattaaactt tctattatgc tgactaaaat   360
ggaagtgatc accaaaggct atttctgatt atataatcta gtcattactc gctcgag     417

<210> SEQ ID NO 13
<211> LENGTH: 171
<212> TYPE: DNA
<213> ORGANISM: Artificial Sequence
<220> FEATURE:
<223> OTHER INFORMATION: Synthetic SH3 domain
<220> FEATURE:
<221> NAME/KEY: CDS
<222> LOCATION: (1)..(171)

<400> SEQUENCE: 13 gca gag tat gtg cgg gcc ctc ttt gac ttt aat ggg aat gat gaa gaa     48
Ala Glu Tyr Val Arg Ala Leu Phe Asp Phe Asn Gly Asn Asp Glu Glu
1               5                   10                  15 gat ctt ccc ttt aag aaa gga gac atc ctg aga atc cgg gat aag cct     96
Asp Leu Pro Phe Lys Lys Gly Asp Ile Leu Arg Ile Arg Asp Lys Pro
```

```
                    20                  25                  30
gaa gag cag tgg tgg aat gca gag gac agc gaa gga aag agg ggg atg       144
Glu Glu Gln Trp Trp Asn Ala Glu Asp Ser Glu Gly Lys Arg Gly Met
        35                  40                  45 att cct gtc cct tac gtg gag aag tat                                   171
Ile Pro Val Pro Tyr Val Glu Lys Tyr
 50                  55

<210> SEQ ID NO 14
<211> LENGTH: 57
<212> TYPE: PRT
<213> ORGANISM: Artificial Sequence
<220> FEATURE:
<223> OTHER INFORMATION: Synthetic Construct

<400> SEQUENCE: 14

Ala Glu Tyr Val Arg Ala Leu Phe Asp Phe Asn Gly Asn Asp Glu Glu
 1               5                  10                  15

Asp Leu Pro Phe Lys Lys Gly Asp Ile Leu Arg Ile Arg Asp Lys Pro
                20                  25                  30

Glu Glu Gln Trp Trp Asn Ala Glu Asp Ser Glu Gly Lys Arg Gly Met
        35                  40                  45

Ile Pro Val Pro Tyr Val Glu Lys Tyr
 50                  55

<210> SEQ ID NO 15
<211> LENGTH: 33
<212> TYPE: DNA
<213> ORGANISM: Artificial Sequence
<220> FEATURE:
<223> OTHER INFORMATION: Synthetic SH3-binding ligand
<220> FEATURE:
<221> NAME/KEY: CDS
<222> LOCATION: (1)..(33)

<400> SEQUENCE: 15 cct cca cct gct ctg cca cct aag aga agg aga                            33
Pro Pro Pro Ala Leu Pro Pro Lys Arg Arg Arg
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Pro Pro Pro Ala Leu Pro Pro Lys Arg Arg Arg
 1               5                  10

<210> SEQ ID NO 17
<211> LENGTH: 269
<212> TYPE: DNA
<213> ORGANISM: Saccharomyces cerevisiae

<400> SEQUENCE: 17
tctttgaaaa gataatgtat gattatgctt tcactcatat ttatacagaa acttgatgtt      60
ttctttcgag tatatacaag gtgattacat gtacgtttga agtacaactc tagattttgt    120
agtgccctct tgggctagcg gtaaaggtgc gcattttttc acaccctaca atgttctgtt    180
caaaagattt tggtcaaacg ctgtagaagt gaaagttggt gcgcatgttt cggcgttcga    240
aacttctccg cagtgaaaga taaatgatc                                      269
```

```
<210> SEQ ID NO 18
<211> LENGTH: 14
<212> TYPE: DNA
<213> ORGANISM: Saccharomyces cerevisiae

<400> SEQUENCE: 18 tgtttttat gtct                                                        14

<210> SEQ ID NO 19
<211> LENGTH: 20
<212> TYPE: DNA
<213> ORGANISM: Saccharomyces cerevisiae

<400> SEQUENCE: 19 aacccagtg cctggggtcc                                                  20

<210> SEQ ID NO 20
<211> LENGTH: 20
<212> TYPE: DNA
<213> ORGANISM: Saccharomyces cerevisiae

<400> SEQUENCE: 20
ataacggaat ccaactgggc                                                 20

<210> SEQ ID NO 21
<211> LENGTH: 10
<212> TYPE: DNA
<213> ORGANISM: Saccharomyces cerevisiae

<400> SEQUENCE: 21
tgautgcatg                                                            10

<210> SEQ ID NO 22
<211> LENGTH: 10
<212> TYPE: DNA
<213> ORGANISM: Saccharomyces cerevisiae

<400> SEQUENCE: 22
catgcagtca                                                            10

<210> SEQ ID NO 23
<211> LENGTH: 10
<212> TYPE: DNA
<213> ORGANISM: Saccharomyces cerevisiae

<400> SEQUENCE: 23
tgactgcatg                                                            10

<210> SEQ ID NO 24
<211> LENGTH: 23
<212> TYPE: DNA
<213> ORGANISM: Saccharomyces cerevisiae

<400> SEQUENCE: 24
tgacttgact gcatgacctg act                                             23

<210> SEQ ID NO 25
<211> LENGTH: 23
<212> TYPE: DNA
<213> ORGANISM: Saccharomyces cerevisiae

<400> SEQUENCE: 25
```

```
                                        -continued agtcaggtca tgcagtcaag tca                                          23

<210> SEQ ID NO 26
<211> LENGTH: 10
<212> TYPE: RNA
<213> ORGANISM: Saccharomyces cerevisiae

<400> SEQUENCE: 26
ugacugcaug                                                         10

<210> SEQ ID NO 27
<211> LENGTH: 13
<212> TYPE: DNA
<213> ORGANISM: Saccharomyces cerevisiae

<400> SEQUENCE: 27
gcatgacctg act                                                     13
```

METHOD FOR MODIFYING GENOME SEQUENCE TO INTRODUCE SPECIFIC MUTATION TO TARGETED DNA SEQUENCE BY BASE-REMOVAL REACTION, AND MOLECULAR COMPLEX USED THEREIN

CROSS-REFERENCE TO RELATED APPLICATIONS

This patent application is the U.S. national phase of International Patent Application No. PCT/JP2015/080958, filed Nov. 2, 2015, which claims the benefit of Japanese Patent Application No. 2014-224745, filed on Nov. 4, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 49,254 bytes ASCII (Text) file named "728697Replacement-SequenceListing.txt," created Dec. 27, 2018.

TECHNICAL FIELD

The present invention relates to a modification method of a genome sequence, which enables modification of a nucleic acid base in a particular region of a genome, without cleaving double stranded DNA (no cleavage or single strand cleavage), or inserting a foreign DNA fragment, but utilizing a base excision reaction, and a complex of a nucleic acid sequence-recognizing module and DNA glycosylase to be used therefor.

BACKGROUND ART

In recent years, genome editing is attracting attention as a technique for modifying the object gene and genome region in various species. Conventionally, as a method of genome editing, a method utilizing an artificial nuclease comprising a molecule having a sequence-independent DNA cleavage ability and a molecule having a sequence recognition ability in combination has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1), a method of cleaving or modifying a target gene in a particular nucleotide sequence or a site adjacent thereto by using TALEN wherein a transcription activator-like (TAL) effector which is a DNA binding module that the plant pathogenic bacteria *Xanthomonas* has, and a DNA endonuclease are linked (patent document 2), a method utilizing CRISPR-Cas9 system wherein DNA sequence CRISPR (Clustered Regularly interspaced short palindromic repeats) that functions in an acquired immune system possessed by eubacterium and archaebacterium, and nuclease Cas (CRISPR-associated) protein family having an important function along with CRISPR are combined (patent document 3) and the like have been reported. Furthermore, a method of cleaving a target gene in the vicinity of a particular sequence, by using artificial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

These genome editing techniques basically presuppose double stranded DNA breaks (DSB). However, since they include unexpected genome modifications, side effects such as strong cytotoxicity, chromosomal rearrangement and the like occur, and they have common problems of impaired reliability in gene therapy, extremely small number of surviving cells by nucleotide modification, and difficulty in genetic modification itself in primate ovum and unicellular microorganisms.

On the other hand, as a method of performing nucleotide modification without causing DSB, utilization of DNA glycosylase has been proposed. For example, patent document 5 describes that mutant DNA glycosylase having an activity to eliminate a thymine or cytosine base from a single stranded or double stranded DNA (TDG activity or CDG activity) was obtained by introducing mutation into human uracil-DNA glycosylase (UDG) and, using the enzyme, the efficiency of mutation induction in *Escherichia coli* was improved.

Furthermore, patent document 6 and non-patent document 2 describe that targeted nucleotide modification into a genome region having a Tet operator (TetO) DNA sequence specifically recognized by TetR is possible by using a fusion protein of yeast 3-methyladenine-DNA glycosylase (MAGI) and Tet repressor protein (TetR). However, MAGI essentially removes a special DNA base that was injured by alkylation and the like, which is mainly 3-methyladenine, and the ability to remove a base from normal bases, particularly base pairs without a mismatch, is extremely low. Therefore, it is difficult to observe the effect of mutation introduction by MAGI in normal cells, and a detectable mutation rate has been obtained only by overexpressing MAGI in cells with disrupted genes of base excision repair system. In addition, when the DNA-repair system is weakened, the mutation rate of the entire genome also increases, which makes practicalization a far goal. However, when a mutant UDG having CDG activity to act on a normal cytosine base was used for this system instead of MAGI, the efficiency of mutation induction did not increase (patent document 6, non-patent document 2).

DOCUMENT LIST

Patent Documents
patent document 1: JP-B-4968498
patent document 2: National Publication of International Patent
Application No. 2013-513389
patent document 3: National Publication of International Patent
Application No. 2010-519929
patent document 4: JP-A-2013-128413
patent document 5: WO 97/25416
patent document 6: WO 2014/127287
Non-Patent Documents
non-patent document 1: Kelvin M Esvelt, Harris H Wang (2013) Genome-scale engineering for systems and synthetic biology, Molecular Systems Biology 9: 641
non-patent document 2: Shwan P. Finney-Manchester, Narendra Maheshri, (2013) Harnessing mutagenic homologous recombination for targeted mutagenesis in vivo by TaGTEAM, Nucleic Acids Research 41(9): e99

SUMMARY OF THE INVENTION

Problems to be Solved by the Invention

An object of the present invention is to provide a novel method of genome editing for modifying a nucleic acid base of a particular sequence of a gene without DSB or insertion of foreign DNA fragment, i.e., by non-cleavage of a double stranded DNA or single strand cleavage, and a complex of a nucleic acid sequence-recognizing module and a mutation introducing enzyme therefor.

Means of Solving the Problems

The present inventors have already reported that they have successfully modified, without DSB, a genome sequence by nucleic acid base conversion in a region containing a particular DNA sequence, by using deaminase that catalyzes a deamination reaction and linking the enzyme and a molecule having a DNA sequence recognition ability (WO 2015/133554). In expectation of affording a mutation introduction tendency different from that of deaminase and the like, the present invention is based on an idea of causing a base excision reaction by hydrolysis of N-glycosidic bond of DNA, and then inducing mutation introduction in a repair process of cells. Thus, attempts have been made to use an enzyme having CDG activity or TDG activity, which is a mutant of yeast mitochondrial uracil-DNA glycosylase (UNG 1), as an enzyme that performs such base excision reaction.

The present inventors assumed that one of the reasons for a failure to improve efficiency of mutation induction by conventional methods (e.g., patent document 6 and non-patent document 2) even by using mutant UDG having CDG activity is that the enzyme causes base excision everywhere in the double stranded DNA, which in turn causes high cytotoxicity and makes it difficult to express the enzyme protein itself. Under such hypothesis, the present inventors modified a genome sequence by nucleic acid base conversion in a region containing a particular DNA sequence, by introducing a mutation that lowers an action on a DNA having an unrelaxed double helix structure (unrelaxed (double-helical) DNA) into a mutant UDG having CDG activity or TDG activity, and linking the mutant enzyme and a molecule having a DNA sequence recognition ability.

To be specific, CRISPR-Cas system (CRISPR-mutant Cas) was used. That is, a DNA encoding an RNA molecule wherein genome specific CRISPR-RNA:crRNA (gRNA) containing a sequence complementary to a target sequence of a gene to be modified is linked to an RNA (trans-activating crRNA: tracrRNA) for recruiting Cas protein was produced, a DNA wherein a DNA encoding a mutant Cas protein (dCas) wherein cleavage ability of both strands of a double stranded DNA is inactivated and a mutant CDG or TDG gene are linked was produced, and these DNAs were introduced into a host yeast cell containing a gene to be modified. As a result, mutation could be introduced randomly within the range of several hundred nucleotides of the object gene including the target sequence. Furthermore, mutation could be introduced extremely efficiently by targeting multiple regions in the object gene. That is, a host cell introduced with DNA was seeded in a nonselective medium, and the sequence of the object gene was examined in randomly selected colonies. As a result, introduction of mutation was confirmed in almost all colonies. The efficiency of mutation induction was further improved by coexpressing mutant AP endonuclease lacking its function as an enzyme of a base excision repair system, thereby increasing the frequency of repair errors in an abasic site (AP site).

It was also confirmed that a system using a heterogenous mutant UDG also functions in yeast. Unexpectedly, UDG derived from vaccinia virus (vvUDG) does not cause cytotoxicity even in the absence of introduction of mutation that lowers the action on an unrelaxed double helix structure of DNA, and mutant UDG introduced solely with mutations that change substrate specificity rather showed higher efficiency of mutation induction. That is, vvUDG was suggested to be an enzyme having a natively low action on DNA having an unrelaxed double-helix structure. This was also supported by the fact that the mutated sites by vvUDG are concentrated in a particular base within the target sequence (i.e., single strand part). In addition, the activity of vvUDG could be increased by co-expressing A20, which is known as a cofactor.

The present inventors obtained an idea of utilization of split Cas9 system as a means to decrease non-specific mutation by UDG, in addition to the introduction of mutation into the enzyme. Split Cas9 is a variant of Cas9, which is designed to function only when N-terminal fragment and C-terminal fragment split from Cas9 protein are associated with gRNA (Nat Biotechnol. 33(2): 139-142 (2015); PNAS 112(10): 2984-2989 (2015)). The present inventors constructed a system expressing split dCas9-mutant UNG1 as one fusion protein consisting of N-terminal fragment of dCas9-N-terminal fragment of mutant UNG1-C-terminal fragment of dCas9-C-terminal fragment of mutant UNG1, and a system separately expressing N-terminal fragment of dCas9-C-terminal fragment of mutant UNG1, and N-terminal fragment of mutant UNG1-C-terminal fragment of dCas9, and then examined the frequency of mutation and non-specific mutation at the target site by using a sequence in the Can1 gene as a target, as well as cell proliferation. As a result, in any system, the cell survival rate on a nonselective medium is hardly different between mutant UNG1 introduced only with mutation (N222D) that imparts CDG activity, and mutant UNG1 further introduced with mutation (R308C) that decreases the action on an unrelaxed double helix structure of DNA, and the cytotoxicity was markedly reduced by utilization of the split enzyme. When split enzyme was used, the frequency of non-specific mutation using thialysine resistance as an index was also reduced without depending on the presence or absence of R308 mutation. The efficiency of mutation induction at the original target site rather decreased, since addition of the R308Q mutation also decreases the CDG activity. It was suggested, therefore, a mutation that reduces the action on an unrelaxed double helix structure of DNA is preferably not added to UDG when a split enzyme is used.

The present inventor have conducted further studies based on these findings and completed the present invention.

Therefore, the present invention is as described below.

[1] A method of modifying a targeted site of a double stranded DNA in a cell, comprising a step of contacting a complex wherein a nucleic acid sequence-recognizing module that specifically binds to a target nucleotide sequence in a given double stranded DNA and DNA glycosylase with sufficiently low reactivity with a DNA having an unrelaxed double helix structure (unrelaxed DNA) are bonded, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site.

[2] The method of the above-mentioned [1], wherein the aforementioned nucleic acid sequence-recognizing module is selected from the group consisting of a CRISPR-Cas system wherein at least one DNA cleavage ability of Cas is inactivated, a zinc finger motif, a TAL effector and a PPR motif.

[3] The method of the above-mentioned [1], wherein the aforementioned nucleic acid sequence-recognizing module is a CRISPR-Cas system wherein at least one DNA cleavage ability of Cas is inactivated.

[4] The method of the above-mentioned [1] or [2], wherein the double stranded DNA is further contacted with a factor that changes a DNA double stranded structure.

[5] The method of any of the above-mentioned [1]-[4], which uses two or more kinds of nucleic acid sequence-recognizing modules each specifically binding to a different target nucleotide sequence.

[6] The method of the above-mentioned [5], wherein the aforementioned different target nucleotide sequences are present in different genes.

[7] The method of any of the above-mentioned [1]-[6], wherein the aforementioned DNA glycosylase has cytosine-DNA glycosylase (CDG) activity or thymine-DNA glycosylase (TDG) activity.

[8] The method of the above-mentioned [7], wherein the aforementioned DNA glycosylase having CDG activity or TDG activity is a mutant of uracil-DNA glycosylase (UDG).

[9] The method of any of the above-mentioned [1]-[8], further comprising contacting the double stranded DNA with an AP endonuclease having binding capacity to an abasic site but lacking nuclease activity.

[10] The method of any of the above-mentioned [1]-[9], wherein the aforementioned DNA glycosylase has natively low reactivity with a DNA having an unrelaxed double helix structure.

[11] The method of the above-mentioned [10], wherein the aforementioned DNA glycosylase is a mutant of uracil-DNA glycosylase (UDG) derived from a virus belonging to Poxviridae and having CDG activity or TDG activity.

[12] The method of the above-mentioned [11], wherein the double stranded DNA is further contacted with A20 protein.

[13] The method of any of the above-mentioned [1]-[9], wherein the aforementioned DNA glycosylase is a mutant having reduced reactivity with a DNA having an unrelaxed double helix structure (unrelaxed DNA) as compared to a wild-type one.

[14] The method of any of the above-mentioned [1]-[9], wherein the aforementioned DNA glycosylase, and an element of the aforementioned nucleic acid sequence-recognizing module which is directly bonded to the DNA glycosylase are respectively split into two fragments, the fragments of either of the DNA glycosylase and the element are respectively linked to the fragments of the other to provide two partial complexes, and when the partial complexes are refolded with each other, the nucleic acid sequence-recognizing module is capable of specifically binding to the target nucleotide sequence and the specific bond enables the DNA glycosylase to exhibit enzyme activity.

[15] The method of the above-mentioned [14], wherein the element of the nucleic acid sequence-recognizing module which is directly bonded to the aforementioned DNA glycosylase is a Cas protein wherein at least one of the DNA cleavage abilities is inactivated.

[16] The method of the above-mentioned [14] or [15], wherein the aforementioned two partial complexes are provided as separate molecule complexes, and are refolded by association thereof in the cell.

[17] The method of any of the above-mentioned [1]-[16], wherein the double stranded DNA is contacted with the complex by introducing a nucleic acid encoding the complex into a cell having the double stranded DNA.

[18] The method of the above-mentioned [17], wherein the aforementioned cell is a prokaryotic cell.

[19] The method of the above-mentioned [17], wherein the aforementioned cell is a eukaryotic cell.

[20] The method of the above-mentioned [17], wherein the aforementioned cell is a microbial cell.

[21] The method of the above-mentioned [17], wherein the aforementioned cell is a plant cell.

[22] The method of the above-mentioned [17], wherein the aforementioned cell is an insect cell.

[23] The method of the above-mentioned [17], wherein the aforementioned cell is an animal cell.

[24] The method of the above-mentioned [17], wherein the aforementioned cell is a vertebrate cell.

[25] The method of the above-mentioned [17], wherein the aforementioned cell is a mammalian cell.

[26] The method of any of the above-mentioned [18]-[25], wherein the aforementioned cell is a polyploid cell, and all of the targeted sites in alleles on a homologous chromosome are modified.

[27] A nucleic acid-modifying enzyme complex wherein a nucleic acid sequence-recognizing module that specifically binds to a target nucleotide sequence in a given double stranded DNA and DNA glycosylase with sufficiently low reactivity with a DNA having an unrelaxed double helix structure (unrelaxed DNA) are bonded, which converts one or more nucleotides in the targeted site to other one or more nucleotides or deletes one or more nucleotides, or inserts one or more nucleotides into said targeted site, without cleaving at least one strand of said double stranded DNA in the targeted site.

[28] A nucleic acid encoding the nucleic acid-modifying enzyme complex of the above-mentioned [27].

Effect of the Invention

According to the genome editing technique of the present invention, since it does not accompany insertion of a foreign DNA or double stranded DNA breaks, the technique is superior in safety, and has no small possibility of affording a solution to cases causing biological or legal disputes on conventional methods as relating to gene recombination. It is also possible to set an appropriate range of mutation introduction up to the range of several hundred bases including the target sequence, and the technique can also be applied to topical evolution induction by introduction of random mutation into a particular restricted region, which has been almost impossible heretofore.

DESCRIPTION OF EMBODIMENTS

Figure 1:
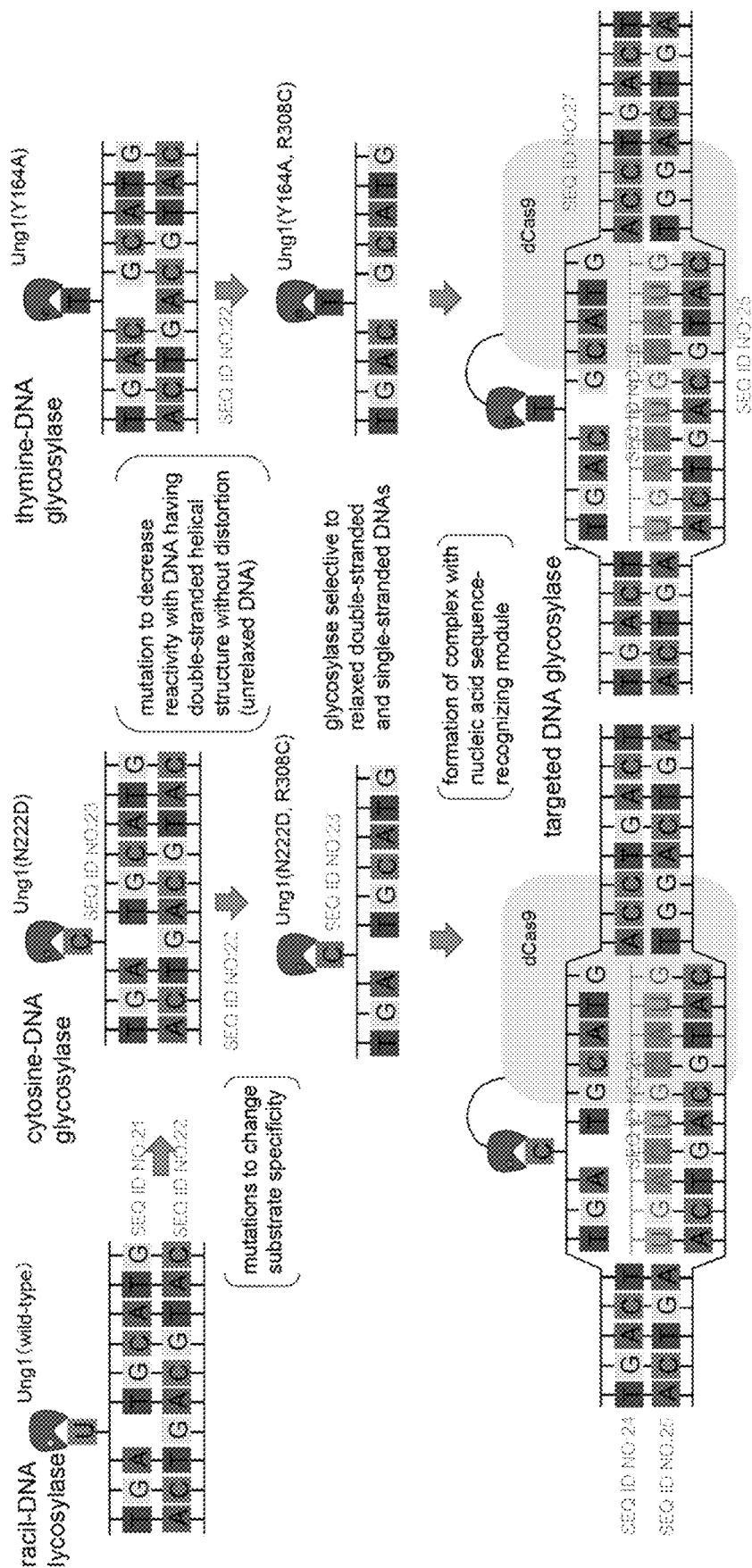
FIG. 1 is a schematic showing of the mechanism of DNA sequence specific targeting of uracil-DNA glycosylase mutant.

The present invention provides a method of modifying a nucleotide of a targeted site of a double stranded DNA by utilizing an error in base excision repair (BER) of cells, by excising a base from a nucleotide in a single strand region or in a region in which the double helix structure is relaxed in the target nucleotide sequence of the double stranded DNA and in the vicinity thereof, without cleaving at least one strand of the double stranded DNA to be modified. The method is characterized in that it contains a step of contacting a complex wherein the nucleic acid sequence-recognizing module that specifically binds to the target nucleotide sequence in the double stranded DNA, and DNA glycosylase with sufficiently low reactivity with a DNA having an unrelaxed double helix structure are bonded with the double stranded DNA to convert the targeted site, i.e., the target nucleotide sequence and nucleotides in the vicinity thereof, to other nucleotides or delete same, or insert one or more nucleotides into the targeted site.

In the present invention, the "modification" of a double stranded DNA means that a nucleotide (e.g., dC) on a DNA strand is converted to other nucleotide (e.g., dT, dA or dG), or deleted, or a nucleotide or a nucleotide sequence is inserted between certain nucleotides on a DNA strand.

While the double stranded DNA to be modified is not particularly limited, it is preferably a genomic DNA. The "targeted site" of a double stranded DNA means the whole or partial "target nucleotide sequence", which a nucleic acid sequence-recognizing module specifically recognizes and binds to, or the vicinity of the target nucleotide sequence (one or both of 5' upstream and 3' downstream), and the range thereof can be appropriately adjusted between 1 base and several hundred bases according to the object.

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a DNA glycosylase linked to the module to specifically act on a targeted site of a double stranded DNA.

In the present invention "DNA glycosylase" means an enzyme that hydrolyzes N-glycosidic bond of DNA. DNA glycosylase originally plays a role of eliminating injured bases from DNA in BER. In the present invention, DNA glycosylase capable of acting on normal bases (i.e., dC, dT, dA and dG, or those after epigenetic modification) in DNA is preferable. A mutant DNA glycosylase which natively does not react with a normal base or has low reactivity but which acquired reactivity or has improved reactivity with a normal base by mutation is encompassed in the DNA glycosylase in the present invention and can be preferably used. An abasic site (apurinic/apyrimidic (AP) site) resulting from the base excision reaction by the enzyme is treated with an enzyme at the downstream of the BER pathway, such as AP endonuclease, DNA polymerase, DNA ligase and the like.

With "sufficiently low reactivity with a DNA having an unrelaxed double helix structure" means that a base excision reaction in a region where a DNA having an unrelaxed double helix structure is formed is performed only at a frequency sufficient to suppress cytotoxicity to a level uninfluential on the survival of the cells. As used herein, a "DNA having an unrelaxed double helix structure" refers to having formed a firm double helix structure (namely, unrelaxed double-helical DNA (or simply unrelaxed DNA)), and does not include the state of single strand DNA from completely dissociated pairing bases, and the state of double strands in an unwound and relaxed double helix structure forming base pairs (relaxed double-stranded DNA). Examples of the DNA glycosylase with sufficiently low reactivity with a DNA having an unrelaxed double helix structure include DNA glycosylase with natively sufficiently low reactivity with a DNA having an unrelaxed double helix structure, mutant DNA glycosylase introduced with a mutation to decrease reactivity with a DNA having an unrelaxed double helix structure as compared to wild-type and the like. Furthermore, DNA glycosylase which is a split enzyme designed to be split into two fragments, wherein respective fragments are bonded to either one of the nucleic acid sequence-recognizing module split into two to form two complexes, when the both complexes are refolded, the nucleic acid sequence-recognizing module can be specifically bonded to the target nucleotide sequence, and, due to the specific bond, the DNA glycosylase can catalyze the base excision reaction is also encompassed in the "DNA glycosylase with sufficiently low reactivity with a DNA having an unrelaxed double helix structure" in the present invention.

In the present invention, the "nucleic acid-modifying enzyme complex" means a molecule complex comprising a complex wherein the above-mentioned nucleic acid sequence-recognizing module and a DNA glycosylase with sufficiently low reactivity with a DNA having an unrelaxed double helix structure are linked, which molecule complex is imparted with a particular nucleotide sequence recognition ability, and an activity to catalyze a base excision reaction of nucleic acid. The "complex" here encompasses not only one constituted of multiple molecules, but also one having a nucleic acid sequence-recognizing module and DNA glycosylase in a single molecule, like a fusion protein. In addition, the "nucleic acid-modifying enzyme complex" in the present invention also encompasses a molecule complex in which nucleic acid sequence-recognizing module split into two fragments and either fragments of DNA glycosylase split into two fragments are linked to each other to form two "partial complexes", and the molecule complex acquires a nucleotide sequence recognition ability and a base excision reaction catalyst activity when the partial complexes are refolded with each other.

While DNA glycosylase to be used in the present invention is not particularly limited as long as it can hydrolyze N-glycosidic bond of DNA to catalyze a reaction for releasing a base, DNA glycosylase capable of acting on normal bases (i.e., dC, dT, dA and dG, or those after epigenetic modification, for example, 5-methylcytosine etc.) in DNA is preferable to increase versatility as a genome editing technique. Examples of such enzyme include an enzyme having CDG activity to catalyze a reaction for releasing cytosine, an enzyme having TDG activity to catalyze a reaction for releasing thymine, an enzyme having activity to catalyze a reaction for releasing 5-methylcytosine (5-mCDG activity) and the like. While DNA glycosylase natively having CDG activity has not been reported to date, in almost all species, a mutant UDG having CDG activity or TDG activity that recognizes cytidine or thymidine as a substrate can be obtained by introducing a mutation into a particular amino acid residue of UNG known as the major UDG responsible for the removal of uracil incorporated in DNA (in the case of eucaryote, it has two splice variants of mitochondrial localization UNG1 and nuclear localization UNG2, which have a common amino acid sequence except N-terminal sequence containing each oraganelle localization signal) (see FIG. 1, upper panel). More specifically, for example, in the case of UNG1 derived from yeast (SEQ ID NO: 2; GenBank accession No. NP_013691), CDG activity can be imparted by substituting the 222nd asparagine from the N-terminal with aspartic acid (the mutant is also referred to as N222D), and TDG activity can be imparted by substituting the 164th tyrosine with alanine (the mutant is also referred to as Y164A) (Kavli B. et al., EMBO J. (1996) 15(13): 3442-7). The present inventors have newly found that TDG activity higher than that of Y164A mutant can be imparted by substituting the 164th tyrosine with glycine (the mutant is also referred to as Y164G). Furthermore, since cytosine is obtained by substituting the carbonyl group at the 4-position of uracil with an amino group and thymine is equivalent to uracil in which the 5-position is methylated, DNA glycosylase having an activity to release 5-methylcytosine, derived from methylation of the 5-position of cytosine, from DNA (5-mCDG activity) can be obtained by introducing double mutation into the 222nd asparagine residue and the 164th tyrosine residue (e.g., N222D/Y164A or N222D/Y164G). Since base excision of 5-methylcytosine can change the methylation state of the genomic DNA, the genome editing technique of the present invention also enables epigenome editing to change epigenetic modification.

When UNG2 is used, mutant UNG having CDG activity, TDG activity or 5-mCDG activity can be obtained by introducing similar mutation into the amino acid residue corresponding to the above-mentioned mutated site.

In the mutant UNG, the above-mentioned site may be substituted with an amino acid other than the above-mentioned amino acid, or the mutation may be introduced into a site other than the above-mentioned site, as long as it can act on a normal base. Whether the mutant UNG can act on a normal base can be confirmed by the method described in, for example, Kavli B. et al., EMBO J. (1996) 15(13): 3442-7.

While the derivation of UNG is not particularly limited, for example, ung derived Escherichia coli (Varshney, U. et al. (1988) J. Biol. Chem., 263, 7776-7784), UNG1 or UNG2 derived from yeast, mammal (e.g., human, mouse, swine, bovine, horse, monkey etc.) and the like, or UDG derived from virus (e.g., Poxviridae (vaccinia virus etc.), Herpesviridae and the like) can be used. For example, UniprotKB Nos. P13051-2 and P13051-1 can be referred to for the amino acid sequences of human UNG1 and UNG2, respectively. In addition, UniprotKB No. P12295 can be referred to for the amino acid sequence of Escherichia coli (K-12 strain) ung, and UniprotKB No. P20536 can be referred to for the amino acid sequence of vaccinia virus (Copenhagen Strain) UDG. The amino acid sequence of UNG is highly preserved among species, and the corresponding site for mutation can be identified by aligning the amino acid sequence of UNG1 or UNG2 derived from a desired organism with that of the above-mentioned yeast UNG1. For example, in the case of human UNG1, the amino acid corresponding to N222 of yeast UNG1 is the 204th asparagine (N204), and the amino acid corresponding to Y164 is the 147th tyrosine (Y147). In the case of Escherichia coli ung, the amino acid corresponding to N222 of yeast UNG1 is the 123rd asparagine (N123), and the amino acid corresponding to Y164 is the 66th tyrosine (Y66). In the case of UDG derived from Poxviridae virus such as vaccinia virus, smallpoxvirus, monkeypoxvirus, fowlpox virus, swinepox virus, rabbit fibroma virus, the amino acid corresponding to N222 of yeast UNG1 is the 120th asparagine (N120), and the amino acid corresponding to Y164 is the 70th tyrosine (Y70).

While UNG can remove uracil from single stranded DNA and double stranded DNA, it has higher affinity for single stranded DNA. This tendency is also found in the above-mentioned mutant UNG conferred with CDG activity and TDG activity. However, since cytosine and thymine exist everywhere in the genomic DNA, mutant UNG having CDG activity or TDG activity acts, unlike wild-type UNG that exclusively uses, as a substrate, uracil which is rarely introduced into genomic DNA by an error on replication or deamination of cytosine, on any site in the nucleotide sequence targeted by a nucleic acid sequence-recognizing module and double stranded DNA in the vicinity thereof to remove cytosine or thymine, thus causing strong cytotoxicity. Therefore, DNA glycosylase to be used in the present invention is required to show sufficiently low reactivity with a DNA having an unrelaxed double helix structure. When mutant UNG is used as DNA glycosylase, the cytotoxicity by the enzyme can be avoided by further introducing a mutation that decreases reactivity with a DNA having an unrelaxed double helix structure to make a base excision reaction by mutant UNG having CDG activity or TDG activity more selective to the region of a relaxed double-stranded or single stranded DNA (see FIG. 1, middle panel). Specifically, for example, in the case of UNG, a mutation that decreases the reactivity with U-A 25 mer double stranded DNA to not more than 1/20, more preferably not more than 1/50, further preferably not more than 1/100, in vitro, that of the wild-type can be mentioned. However, as long as the reactivity with a DNA having an unrelaxed double helix structure is decreased to a level free from lethal cytotoxicity in vivo, it is not limited by the reactivity in vitro. Whether the DNA glycosylase to be used has "sufficiently low reactivity with a DNA having an unrelaxed double helix structure" can be confirmed, for example, by inserting the DNA glycosylase into the construct described in FIG. 2, introducing the construct together with the guide RNA into the object cell by the method described in Example 1, culturing the obtained transformant, and verifying the survivability thereof. Alternatively, a candidate of DNA glycosylase with "sufficiently low reactivity with a DNA having an unrelaxed double helix structure" can also be screened for by evaluating, as one of the criteria, the reactivity with a double stranded DNA oligomer in vitro by the method described in Chen, C. Y. et al. DNA Repair (Amst) (2005) 4(7): 793-805.

As a DNA glycosylase fulfilling the above-mentioned conditions in the case of, for example, UNG1 derived from yeast (SEQ ID NO: 2), a mutant in which the 304th leucine from the N-terminal is substituted with alanine can be mentioned (the mutant is also referred to as L304A) (Slupphaug, G. et al. Nature (1996) 384(6604): 87-92). Alternatively, a mutant in which the 308th arginine is substituted with glutamic acid or cysteine (the mutants are also referred to as R308E, R308C, respectively) also shows remarkably decreased reactivity with a DNA having an unrelaxed double helix structure (Chen, C. Y. et al. DNA Repair (Amst) (2005) 4(7): 793-805). When a different species derived from UNG is used, the corresponding site for mutation can be identified by aligning the amino acid sequence of UNG1 or UNG2 derived from a desired organism with that of the above-mentioned yeast UNG1. For example, in the case of human UNG1, the amino acid corresponding to L304 of yeast UNG1 is the 272nd leucine (L272), and the amino acid corresponding to R308 is the 276th arginine (R276). In the case of *Escherichia coli* ung, the amino acid corresponding to L304 of yeast UNG1 is the 191st leucine (L191), and the amino acid corresponding to R308 is the 195th arginine (R195). In the case of vaccinia virus UDG, the amino acid corresponding to R308 of yeast UNG1 is the 187th arginine (R187).

The substrate specificity of UNG1(ung) to yeast (*Saccharomyces cerevisiae*), *Escherichia coli*, human and Poxviridae virus, and the site of mutation that changes the reactivity with a DNA having an unrelaxed double helix structure are shown in Table 1. Mutant amino acid is indicated with one letter, and the number shows the position of mutant amino acid when N-terminal amino acid is 1.

TABLE 1

| yeast | Escherichia coli | human | pox virus | change of mutant form and phenotype |
|---|---|---|---|---|
| Y164 | Y66 | Y147 | Y70 | recognizes thymine by mutation to A, G |
| N222 | N123 | N204 | N120 | recognizes cytosine by mutation to D |
| L304 | L191 | L272 | — | reactivity with DNA having unrelaxed double helix structure decreases by mutation to A |

TABLE 1-continued

| yeast | Escherichia coli | human | pox virus | change of mutant form and phenotype |
|---|---|---|---|---|
| R308 | R195 | R276 | R187[a] | reactivity with DNA having unrelaxed double helix structure decreases by mutation to E, C |

[a]In vaccinia virus UDG etc., wild-type itself is considered to have natively low reactivity with DNA having unrelaxed double helix structure.

From the above, preferable examples of the "DNA glycosylase with sufficiently low reactivity with a DNA having an unrelaxed double helix structure" to be used in the present invention include N222D/L304A double mutant, N222D/R308E double mutant, N222D/R308C double mutant, Y164A/L304A double mutant, Y164A/R308E double mutant, Y164A/R308C double mutant, Y164G/L304A double mutant, Y164G/R308E double mutant, Y164G/R308C double mutant, N222D/Y164A/L304A triple mutant, N222D/Y164A/R308E triple mutant, N222D/Y164A/R308C triple mutant, N222D/Y164G/L304A triple mutant, N222D/Y164G/R308E triple mutant, N222D/Y164G/R308C triple mutant and the like of yeast UNG1. When different UNG is used instead of yeast UNG1, a mutant having an amino acid corresponding to each of the above-mentioned mutants, which is introduced with a similar mutation, may be used.

Alternatively, as a "DNA glycosylase with sufficiently low reactivity with a DNA having an unrelaxed double helix structure", DNA glycosylase with natively low reactivity with a DNA having an unrelaxed double helix structure, and high selectivity to relaxed double stranded or single stranded DNA can also be used. Examples of such DNA glycosylase include SMUG1 having UDG activity (Single strand-selective Monofunctional Uracil-DNA Glycosylase). While a mutation conferring CDG activity or TDG activity to SMUG1 is not known, it has been reported that the SMUG1 is important for removal of uracil resulting from deamination of cytosine (Nilsen, H. et al. EMBO J. (2001) 20: 4278-4286). The present inventors have already developed a method for specifically introducing a mutation into the targeted nucleotide sequence and the vicinity thereof, by combining cytidine deaminase capable of converting cytosine to uracil, and a nucleic acid sequence-recognizing module similar to that in the present invention (WO 2015/133554). By combining with the technique, cytosine can be artificially converted to uracil in the targeted site in genomic DNA, after which SMUG1 can be further reacted to release the uracil from DNA. While the derivation of SMUG1 is not particularly limited, for example, SMUG1 derived from *Escherichia coli*, yeast, mammal (e.g., human, mouse, swine, bovine, horse, monkey etc.) and the like can be used. For example, UniprotKB No. Q53HC7-1 and Q53HV7-2 can be referred to for the two amino acid sequences of the two isoforms of human SMUG1. In addition, while the derivation of cytidine deaminase is not particularly limited, for example, Petromyzon marinus-derived PmCDA1 (Petromyzon marinus cytosine deaminase 1), or AID (Activation-induced cytidine deaminase; AICDA) derived from mammal (e.g., human, swine, bovine, horse, monkey etc.) can be used. For example, GenBank accession No. EF094822 and AB015149 can be referred to for the base sequence and the amino acid sequence of PmCDA1 cDNA, and GenBank accession No. NM 020661 and NP 065712 can be referred to for the base sequence and the amino acid sequence of human AID cDNA.

In another preferable embodiment, as the DNA glycosylase with natively low reactivity with a DNA having an unrelaxed double helix structure, UDG derived from virus belonging to Poxviridae such as vaccinia virus and the like can be mentioned. As shown in the below-mentioned Examples, vaccinia virus-derived UDG (vvUDG) is considered to be sufficiently low in the reactivity with a DNA having an unrelaxed double helix structure to a level free from toxicity in a host cell, because it shows growth equivalent to that in yeast UNG1 and *Escherichia coli* ung, introduced with a mutation that decreases reactivity with a DNA having an unrelaxed double helix structure (e.g., R187C), on a nonselective medium, even when such mutation is not introduced. When UDG derived from Poxviridae virus such as vvUDG and the like is used as a DNA glycosylase, a mutation (e.g., R187C) corresponding to the mutation that decreases reactivity with a DNA having an unrelaxed double helix structure in yeast UNG1 can be further introduced. However, when such mutation decreases the CDG activity (N120D) and TDG activity (Y70A, Y70G) of UDG, it is desirably avoided. From the above, preferable examples of UDG derived from Poxviridae virus such as vvUDG to be used in the present invention include N120D mutant, Y70G or Y70A mutant, N120D/Y70G double mutant or N120D/Y70A double mutant and the like.

When UDG derived from Poxviridae virus such as mutant vvUDG and the like is used as the DNA glycosylase, it is preferable to contact A20 protein, which interacts with UDG to form a heterodimer that functions as a processivity factor of viral DNA polymerase, with double stranded DNA together with UDG. Since combined use with A20 protein increases CDG activity or TDG activity of mutant UDG, for example, the efficiency of mutation induction into thymine, of mutant vvUDG having low TDG activity (Y70G) as compared to CDG activity (N120D) can be improved by the combined use with A20 protein. While the derivation of A20 is not particularly limited, for example, A20 derived from virus belonging to Poxviridae such as vaccinia virus, smallpoxvirus, monkeypoxvirus, fowlpox virus, swinepox virus, rabbit fibroma virus can be used. For example, UniprotKB No. P20995 can be referred for the amino acid sequence of vaccinia virus (Copenhagen Strain) A20.

In yet another preferable embodiment, a split enzyme designed such that nucleic acid sequence-recognizing module and DNA glycosylase are each split into two fragments, either fragments are linked to each other to form two partial complexes, these complexes are associated to reconstitute a functional nucleic acid sequence-recognizing module, and the module is bonded to the target nucleotide sequence to reconstitute a functional DNA glycosylase can be used as a DNA glycosylase having low reactivity with a DNA having an unrelaxed double helix structure. In the split enzyme, since the enzyme activity is exhibited only when it is bonded to the target nucleotide sequence, even when the DNA glycosylase itself to be reconstituted does not have a reduced reactivity with a DNA having an unrelaxed double helix structure, it consequently acts selectively on the single stranded DNA or relaxed double stranded DNA part in the target nucleotide sequence and the vicinity thereof. For example, nucleic acid sequence-recognizing module and DNA glycosylase are each split into N-terminal side fragments and C-terminal side fragments, for example, N-terminal side fragments are linked to each other to give a partial complex, C-terminal side fragments are linked to each other to give a partial complex (or N-terminal side fragments of nucleic acid sequence-recognizing module and C-terminal side fragments of DNA glycosylase are linked to give a partial complex, and N-terminal side fragments of DNA glycosylase and C-terminal side fragments of nucleic acid sequence-recognizing module are linked to give a partial complex), and they are associated, whereby functional nucleic acid sequence-recognizing module and functional DNA glycosylase can be reconstituted. The combination of the fragments to be linked is not particularly limited as long as a complex of the functional nucleic acid sequence-recognizing module and the functional DNA glycosylase is reconstituted when the two partial complexes are associated. The two partial complexes may be provided as separate molecules, or may be provided as a single fusion protein by linking them directly or via a suitable linker. The split site in DNA glycosylase is not particularly limited as long as two split fragments can be reconstituted as functional DNA glycosylase, and DNA glycosylase may be split at one site to provide N-terminal side fragment and C-terminal side fragment, or not less than 3 fragments obtained by splitting at two or more sites may be appropriately linked to give two fragments. The three-dimensional structures of various UDG proteins are known, and those of ordinary skill in the art can appropriately select the split sites based on such information. For example, yeast UNG1 (SEQ ID NO: 2) can be split between the 258th amino acid and 259th amino acid from the N-terminal to give N-terminal side fragment (1-258) and C-terminal side fragment (259-359).

As mentioned above, in the base excision repair (BER) mechanism, when a base is excised by DNA glycosylase, AP endonuclease puts a nick in the abasic site (AP site), and exonuclease completely excises the AP site. When the AP site is excised, DNA polymerase produces a new base by using the base of the opposing strand as a template, and DNA ligase finally seals the nick to complete the repair. Mutant AP endonuclease that has lost the enzyme activity but maintains the binding capacity to the AP site is known to competitively inhibit BER. Therefore, when the mutant AP endonuclease is contacted with double stranded DNA together with DNA glycosylase, the repair of the AP site by endogenous BER mechanism in the host cell is inhibited, and the frequency of repair errors, namely, efficiency of mutation induction, is improved. For example, the efficiency of mutation induction into thymine in mutant yeast UNG1 having lower TDG activity (Y164G) as compared to CDG activity (N222D) can be improved by using mutant AP endonuclease in combination. While the derivation of AP endonuclease is not particularly limited, for example, AP endonuclease derived from *Escherichia coli*, yeast, mammal (e.g., human, mouse, swine, bovine, horse, monkey etc.) and the like can be used. For example, UniprotKB No. P27695 can be referred to for the amino acid sequence of human Ape1. Examples of the mutant AP endonuclease that has lost the enzyme activity but maintains the binding capacity to the AP site include proteins having mutated activity site and mutated Mg (cofactor)-binding site. For example, E96Q, Y171A, Y171F, Y171H, D210N, D210A, N212A and the like can be mentioned for human Ape1.

A target nucleotide sequence in a double stranded DNA to be recognized by the nucleic acid sequence-recognizing module in the nucleic acid-modifying enzyme complex of the present invention is not particularly limited as long as the module specifically binds to, and may be any sequence in the double stranded DNA. The length of the target nucleotide sequence only needs to be sufficient for specific binding of the nucleic acid sequence-recognizing module. For example, when mutation is introduced into a particular site in the genomic DNA of a mammal, it is not less than 12 nucleotides, preferably not less than 15 nucleotides, more preferably not less than 17 nucleotides, according to the genome size thereof. While the upper limit of the length is not particularly limited, it is preferably not more than 25 nucleotides, more preferably not more than 22 nucleotides.

As the nucleic acid sequence-recognizing module in the nucleic acid-modifying enzyme complex of the present invention, CRISPR-Cas system wherein at least one DNA cleavage ability of Cas is inactivated (CRISPR-mutant Cas), zinc finger motif, TAL effector and PPR motif and the like, as well as a fragment containing a DNA binding domain of a protein that specifically binds to DNA, such as restriction enzyme, transcription factor, RNA polymerase and the like, and free of a DNA double strand cleavage ability and the like can be used, but the module is not limited thereto. Preferably, CRISPR-mutant Cas, zinc finger motif, TAL effector, PPR motif and the like can be mentioned.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. The above-mentioned patent document 2 can be referred to as for the detail of the production of TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(-2) amino acids of each motif. Motif constitution has no dependency, and is free of interference of motifs on both sides. Therefore, like TAL effector, a PPR protein specific to the target nucleotide sequence can be produced by simply connecting PPR motifs. The above-mentioned patent document 4 can be referred to as for the detail of the production of PPR motif.

When a fragment of restriction enzyme, transcription factor, RNA polymerase and the like is used, since the DNA binding domains of these proteins are well known, a fragment containing the domain and free of a DNA double strand cleavage ability can be easily designed and constructed.

As mentioned above, DNA glycosylase used for the nucleic acid-modifying enzyme complex of the present invention is preferably mutant UDG conferred with CDG activity or TDG activity, more preferably UNG, and it needs to be sufficiently low in the reactivity with a DNA having an unrelaxed double helix structure so that CDG activity or TDG activity will not act on anywhere in the targeted site (see FIG. 1, middle panel). Therefore, the targeted site is desirably in the state of single stranded DNA, or relaxed DNA structure resulting from unwinding of at least firm double helix structure, which enables the DNA glycosylase to act efficiently when brought into contact with DNA glycosylase. When CRISPR-Cas system is used as the nucleic acid sequence-recognizing module, guide RNA complementary to the target nucleotide sequence recognizes the sequence of the object double stranded DNA and specifically forms a hybrid with the target nucleotide sequence, whereby the targeted site becomes the state of single strand or unwound double helix structure (relaxed double stranded) state. Therefore, DNA glycosylase with sufficiently low reactivity with a DNA having an unrelaxed double helix structure selectively acts on cytosine or thymine in the targeted site and can excise the base (see FIG. 1, lower panel). On the other hand, when zinc finger motif, TAL effector, PPR motif and the like are used as the nucleic acid sequence-recognizing module, since the module itself does not have a function to change the structure of double stranded DNA (cause distortion of double helix structure), it is desirable to contact the nucleic acid-modifying enzyme complex of the present invention in combination with a factor (e.g., gyrase, topoisomerase, helicase etc.), which changes the structure of the object double stranded DNA, with the double stranded DNA.

Any of the above-mentioned nucleic acid sequence-recognizing module can be provided as a fusion protein with the above-mentioned DNA glycosylase, or a protein binding domain such as SH3 domain, PDZ domain, GK domain, GB domain and the like and a binding partner thereof may be fused with a nucleic acid sequence-recognizing module and a DNA glycosylase, respectively, and provided as a protein complex via an interaction of the domain and a binding partner thereof. Alternatively, a nucleic acid sequence-recognizing module and a DNA glycosylase may be each fused with intein, and they can be linked by ligation after protein synthesis.

The nucleic acid-modifying enzyme complex of the present invention containing a complex (including fusion protein) wherein a nucleic acid sequence-recognizing module and DNA glycosylase are bonded is contacted with a double stranded DNA (e.g., genomic DNA) by introducing the complex or a nucleic acid encoding the complex into a cell having the object double stranded DNA. In consideration of the introduction and expression efficiency, it is desirable to introduce the nucleic acid-modifying enzyme complex into the cell in the form of a nucleic acid encoding the complex, rather than the complex itself, and allow for expression of the complex in the cell. Also when mutant AP endonuclease, A20 protein and the like are used in combination, it is desirable to introduce them into the cell in the form of a nucleic acid encoding them, and allow for expression of the complex in the cell.

Therefore, the nucleic acid sequence-recognizing module and the DNA glycosylase are preferably prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA. When it is a DNA, it is preferably a double stranded DNA, and provided in the form of an expression vector disposed under regulation of a functional promoter in a host cell. When it is an RNA, it is preferably a single stranded RNA.

When nucleic acid sequence-recognizing module and DNA glycosylase are each split into two fragments, the fragments of either of them are respectively linked to the fragments of the other to provide two partial complexes, for example, a DNA encoding the N-terminal side fragment and a DNA encoding the C-terminal side fragment of the nucleic acid sequence-recognizing module are respectively prepared by the PCR method using suitable primers; and a DNA encoding the N-terminal side fragment and a DNA encoding the C-terminal side fragment of DNA glycosylase are prepared in the same manner and, for example, the DNAs encoding the N-terminal side fragments, and the DNAs encoding the C-terminal side fragments are linked to each other by a conventional method, whereby a DNA encoding the two partial complexes can be produced. Alternatively, a DNA encoding the N-terminal side fragment of the nucleic acid sequence-recognizing module and a DNA encoding the C-terminal side fragment of the DNA glycosylase are linked; and a DNA encoding the N-terminal side fragment of the DNA glycosylase and a DNA encoding the C-terminal side fragment of the nucleic acid sequence-recognizing module are linked, whereby a DNA encoding the two partial complexes can also be produced. The combination of the fragments to be linked is not particularly limited as long as a complex of the functional nucleic acid sequence-recognizing module and the functional DNA glycosylase is reconstituted when the two partial complexes are associated. The two partial complexes are not only expressed as separate molecules, but may also be expressed as a single fusion protein by linking nucleic acids encoding them directly or via a suitable linker, which protein forms a complex of the functional nucleic acid sequence-recognizing module and the functional DNA glycosylase by intramolecular association.

Since the complex of the present invention wherein a nucleic acid sequence-recognizing module and a DNA glycosylase are bonded does not accompany double stranded DNA breaks (DSB), genome editing with low toxicity is possible, and the genetic modification method of the present invention can be applied to a wide range of biological materials. Therefore, the cells to be introduced with nucleic acid encoding nucleic acid sequence-recognizing module and/or DNA glycosylase can encompass cells of any species, from bacterium of *Escherichia coli* and the like which are prokaryotes, cells of microorganism such as yeast and the like which are lower eucaryotes, to cells of vertebrata including mammals such as human and the like, and cells of higher eukaryote such as insect, plant and the like.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding DNA glycosylase can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding UNG1 of yeast can be cloned by designing suitable primers for the upstream and downstream of CDS based on the cDNA sequence (accession No. NM_001182379) registered in the NCBI database, and cloning from yeast-derived mRNA by the RT-PCR method.

A nucleic acid encoding DNA glycosylase with sufficiently low reactivity with a DNA having an unrelaxed double helix structure can be obtained by a site specific mutagenesis method known per se by using the obtained cDNA as a template, and introducing a mutation imparting CDG activity, TDG activity or 5-mCDG activity, and a mutation that decreases reactivity with a DNA having an unrelaxed double helix structure. When DNA glycosylase with natively sufficiently low reactivity with a DNA having an unrelaxed double helix structure, such as vvUDG and the like, only a mutation imparting CDG activity, TDG activity or 5-mCDG activity can be introduced.

The cloned DNA may be directly, or after digestion with a restriction enzyme when desired, or after addition of a suitable linker (e.g., GS linker, GGGAR linker etc.), spacer (e.g., FLAG sequence etc.) and/or a nuclear localization signal (NLS) (each organelle localization signal when the object double stranded DNA is mitochondria or chloroplast DNA), ligated with a DNA encoding a nucleic acid sequence-recognizing module to prepare a DNA encoding a fusion protein. Since UNG1 and UNG2 each have a mitochondria localization signal and a nuclear localization signal on the N-terminal, they may also be utilized as they are. Alternatively, for example, when UNG1 is used for nucleotide modification targeting nuclear genomic DNA, it is possible to remove the mitochondria localization signal and separately link a nuclear localization signal.

Alternatively, a DNA encoding a nucleic acid sequence-recognizing module, and a DNA encoding a DNA glycosylase may be each fused with a DNA encoding a binding domain or a binding partner thereof, or both DNAs may be fused with a DNA encoding a separation intein, whereby the nucleic acid sequence-recognizing conversion module and the DNA glycosylase are translated in a host cell to form a complex. In these cases, a linker and/or a nuclear localization signal can be linked to a suitable position of one of or both DNAs when desired.

A DNA encoding a nucleic acid sequence-recognizing module and a DNA encoding a DNA glycosylase can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (www.kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency.

An expression vector containing a DNA encoding a nucleic acid sequence-recognizing module and/or a DNA glycosylase can be produced, for example, by linking the DNA to the downstream of a promoter in a suitable expression vector.

As the expression vector, *Escherichia coli*-derived plasmids (e.g., pBR322, pBR325, pUC12, pUC13); *Bacillus subtilis*-derived plasmids (e.g., pUB110, pTP5, pC194); yeast-derived plasmids (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as Aphage and the like; insect virus vectors such as baculovirus and the like (e.g., BmNPV, AcNPV); animal virus vectors such as retrovirus, vaccinia virus, adenovirus and the like, and the like are used.

As the promoter, any promoter appropriate for a host to be used for gene expression can be used. In a conventional method using DSB, since the survival rate of the host cell sometimes decreases markedly due to the toxicity, it is desirable to increase the number of cells by the start of the induction by using an inductive promoter. However, since sufficient cell proliferation can also be afforded by expressing the nucleic acid-modifying enzyme complex of the present invention, a constitution promoter can also be used without limitation.

For example, when the host is an animal cell, SRa promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRa promoter and the like are preferable.

When the host is *Escherichia coli*, trp promoter, lac promoter, recA promoter, $\lambda P_L$ promoter, 1pp promoter, T7 promoter and the like are preferable.

When the host is genus *Bacillus*, SPO1 promoter, SPO2 promoter, penP promoter and the like are preferable.

When the host is a yeast, Gal/10 promoter, PHO5 promoter, PGK promoter, GAP promoter, ADH promoter and the like are preferable.

When the host is an insect cell, polyhedrin promoter, P10 promoter and the like are preferable.

When the host is a plant cell, CaMV35S promoter, CaMV19S promoter, NOS promoter and the like are preferable.

As the expression vector, besides those mentioned above, one containing enhancer, splicing signal, terminator, polyA addition signal, a selection marker such as drug resistance gene, auxotrophic complementary gene and the like, replication origin and the like on demand can be used.

An RNA encoding a nucleic acid sequence-recognizing module and/or a DNA glycosylase can be prepared by, for example, transcription to mRNA in a vitro transcription system known per se by using a vector encoding DNA encoding the above-mentioned nucleic acid sequence-recognizing module and/or a DNA glycosylase as a template.

A complex of a nucleic acid sequence-recognizing module and a DNA glycosylase can be intracellularly expressed by introducing an expression vector containing a DNA encoding a nucleic acid sequence-recognizing module and/ or a DNA glycosylase into a host cell, and culturing the host cell.

As the host, genus *Escherichia*, genus *Bacillus*, yeast, insect cell, insect, animal cell and the like are used.

As the genus *Escherichia*, *Escherichia coli* K12•DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used.

As the genus *Bacillus*, *Bacillus subtilis* MI114 [Gene, 24, 255 (1983)], *Bacillus subtilis* 207-21 [Journal of Biochemistry, 95, 87 (1984)] and the like are used.

As the yeast, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71 and the like are used.

As the insect cell when the virus is AcNPV, cells of cabbage armyworm larva-derived established line (*Spodoptera frugiperda* cell; Sf cell), MG1 cells derived from the mid-intestine of *Trichoplusia ni*, High Five™ cells derived from an egg of *Trichoplusia ni*, *Mamestra brassicae*-derived cells, *Estigmena acrea*-derived cells and the like are used. When the virus is BmNPV, cells of *Bombyx mori*-derived established line (*Bombyx mori* N cell; BmN cell) and the like are used as insect cells. As the Sf cell, for example, Sf9 cell (ATCC CRL1711), Sf21 cell [all above, In Vivo, 13, 213-217 (1977)] and the like are used.

As the insect, for example, larva of *Bombyx mori*, *Drosophila*, cricket and the like are used [Nature, 315, 592 (1985)].

As the animal cell, cell lines such as monkey COS-7 cell, monkey Vero cell, Chinese hamster ovary (CHO) cell, dhfr gene-deficient CHO cell, mouse L cell, mouse AtT-20 cell, mouse myeloma cell, rat GH3 cell, human FL cell and the like, pluripotent stem cells such as iPS cell, ES cell and the like of human and other mammals, and primary cultured cells prepared from various tissues are used. Furthermore, zebrafish embryo, *Xenopus oocyte* and the like can also be used.

As the plant cell, suspend cultured cells, callus, protoplast, leaf segment, root segment and the like prepared from various plants (e.g., grain such as rice, wheat, corn and the like, product crops such as tomato, cucumber, egg plant and the like, garden plants such as carnation, *Eustoma russellianum* and the like, experiment plants such as tobacco, *Arabidopsis thaliana* and the like, and the like) are used.

All the above-mentioned host cells may be haploid (monoploid), or polyploid (e.g., diploid, triploid, tetraploid and the like). In the conventional mutation introduction methods, mutation is, in principle, introduced into only one homologous chromosome to produce a hetero gene type. Therefore, desired phenotype is not expressed unless dominant mutation occurs, and homozygousness inconveniently requires labor and time. In contrast, according to the present invention, since mutation can be introduced into any allele on the homologous chromosome in the genome, desired phenotype can be expressed in a single generation even in the case of recessive mutation, which is extremely useful since the problem of the conventional method can be solved.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host.

*Escherichia coli* can be transformed according to the methods described in, for example, Proc. Natl. Acad. Sci. USA, 69, 2110 (1972), Gene, 17, 107 (1982) and the like.

The genus *Bacillus* can be introduced into a vector according to the methods described in, for example, Molecular & General Genetics, 168, 111 (1979) and the like.

A yeast can be introduced into a vector according to the methods described in, for example, Methods in Enzymology, 194, 182-187 (1991), Proc. Natl. Acad. Sci. USA, 75, 1929 (1978) and the like.

An insect cell and an insect can be introduced into a vector according to the methods described in, for example, Bio/Technology, 6, 47-55 (1988) and the like.

An animal cell can be introduced into a vector according to the methods described in, for example, Cell Engineering additional volume 8, New Cell Engineering Experiment Protocol, 263-267 (1995) (published by Shujunsha), and Virology, 52, 456 (1973).

A cell introduced with a vector can be cultured according to a known method according to the kind of the host.

For example, when *Escherichia coli* or genus *Bacillus* is cultured, a liquid medium is preferable as a medium to be used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5-about 8.

As a medium for culturing *Escherichia coli*, for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15-about 43° C. Where necessary, aeration and stirring may be performed.

The genus *Bacillus* is cultured at generally about 30-about 40° C. Where necessary, aeration and stirring may be performed.

Examples of the medium for culturing yeast include Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] and the like. The pH of the medium is preferably about 5-about 8. The culture is performed at generally about 20° C.-about 35° C. Where necessary, aeration and stirring may be performed.

As a medium for culturing an insect cell or insect, for example, Grace's Insect Medium [Nature, 195, 788 (1962)] containing an additive such as inactivated 10% bovine serum and the like as appropriate and the like are used. The pH of the medium is preferably about 6.2-about 6.4. The culture is performed at generally about 27° C. Where necessary, aeration and stirring may be performed.

As a medium for culturing an animal cell, for example, minimum essential medium (MEM) containing about 5-about 20% of fetal bovine serum [Science, 122, 501 (1952)], Dulbecco's modified Eagle medium (DMEM) [Virology, 8, 396 (1959)], RPMI 1640 medium [The Journal of the American Medical Association, 199, 519 (1967)], 199 medium [Proceeding of the Society for the Biological Medicine, 73, 1 (1950)] and the like are used. The pH of the medium is preferably about 6-about 8. The culture is performed at generally about 30° C.-about 40° C. Where necessary, aeration and stirring may be performed.

As a medium for culturing a plant cell, for example, MS medium, LS medium, B5 medium and the like are used. The pH of the medium is preferably about 5-about 8. The culture is performed at generally about 20° C.-about 30° C. Where necessary, aeration and stirring may be performed.

As mentioned above, a complex of a nucleic acid sequence-recognizing module and a DNA glycosylase, i.e., nucleic acid-modifying enzyme complex, can be expressed intracellularly.

An RNA encoding a nucleic acid sequence-recognizing module and/or a DNA glycosylase can be introduced into a host cell by microinjection method, lipofection method and the like. RNA introduction can be performed once or repeated multiple times (e.g., 2-5 times) at suitable intervals.

When a complex of a nucleic acid sequence-recognizing module and a DNA glycosylase is expressed by an expression vector or RNA molecule introduced into the cell, the nucleic acid sequence-recognizing module specifically recognizes and binds to a target nucleotide sequence in the double stranded DNA (e.g., genomic DNA) of interest and, due to the action of the DNA glycosylase linked to the nucleic acid sequence-recognizing module, base excision reaction occurs in the sense strand or antisense strand of the targeted site (whole or partial target nucleotide sequence or appropriately adjusted within several hundred bases including the vicinity thereof) and an abasic site (AP site) is produced in one of the strands of the double stranded DNA. Then, the base excision repair (BER) system in the cell operates, AP endonuclease first recognizes the AP site and cleaves the phosphoric acid bond in one of DNA strand, and exonuclease removes nucleotide subjected to base excision. Then, DNA polymerase inserts a new nucleotide by using the opposing strand DNA as a template and finally DNA ligase repairs the joint. Various mutations are introduced by a repair miss occurring at any stage of this BER. As mentioned above, the BER mechanism in the cell is inhibited, and the frequency of repair miss, and thus, efficiency of mutation induction can be improved by using a mutant AP endonuclease which lost enzyme activity but retains binding capacity to AP site in combination.

As for zinc finger motif, production of many actually functionable zinc finger motifs is not easy, since production efficiency of a zinc finger that specifically binds to a target nucleotide sequence is not high and selection of a zinc finger having high binding specificity is complicated. While TAL effector and PPR motif have a high degree of freedom of target nucleic acid sequence recognition as compared to zinc finger motif, a problem remains in the efficiency since a large protein needs to be designed and constructed every time according to the target nucleotide sequence. Furthermore, since these nucleic acid sequence-recognizing modules do not have a function to change the structure of double stranded DNA (causing strain in the double helix structure), for a DNA glycosylase with sufficiently low reactivity with a DNA having an unrelaxed double helix structure to efficiently act on the targeted site, it is necessary to separately contact a factor that changes the structure of the double stranded DNA with the object double stranded DNA, thus making the operation complicated.

In contrast, since the CRISPR-Cas system recognizes the object double stranded DNA sequence by a guide RNA complementary to the target nucleotide sequence, any sequence can be targeted by simply synthesizing an oligoDNA capable of specifically forming a hybrid with the target nucleotide sequence. Moreover, at the targeted site, since the double stranded DNA is unwound to generate a region having a single stranded structure, and a region adjacent thereto which has a structure of relaxed double stranded DNA, DNA glycosylase can be made to act efficiently in a targeted site-specific manner, without combining factors that change the structure of double stranded DNA.

Therefore, in a more preferable embodiment of the present invention, a CRISPR-Cas system wherein at least one DNA cleavage ability of Cas is inactivated (CRISPR-mutant Cas), is used as a nucleic acid sequence-recognizing module.

Figure 2:
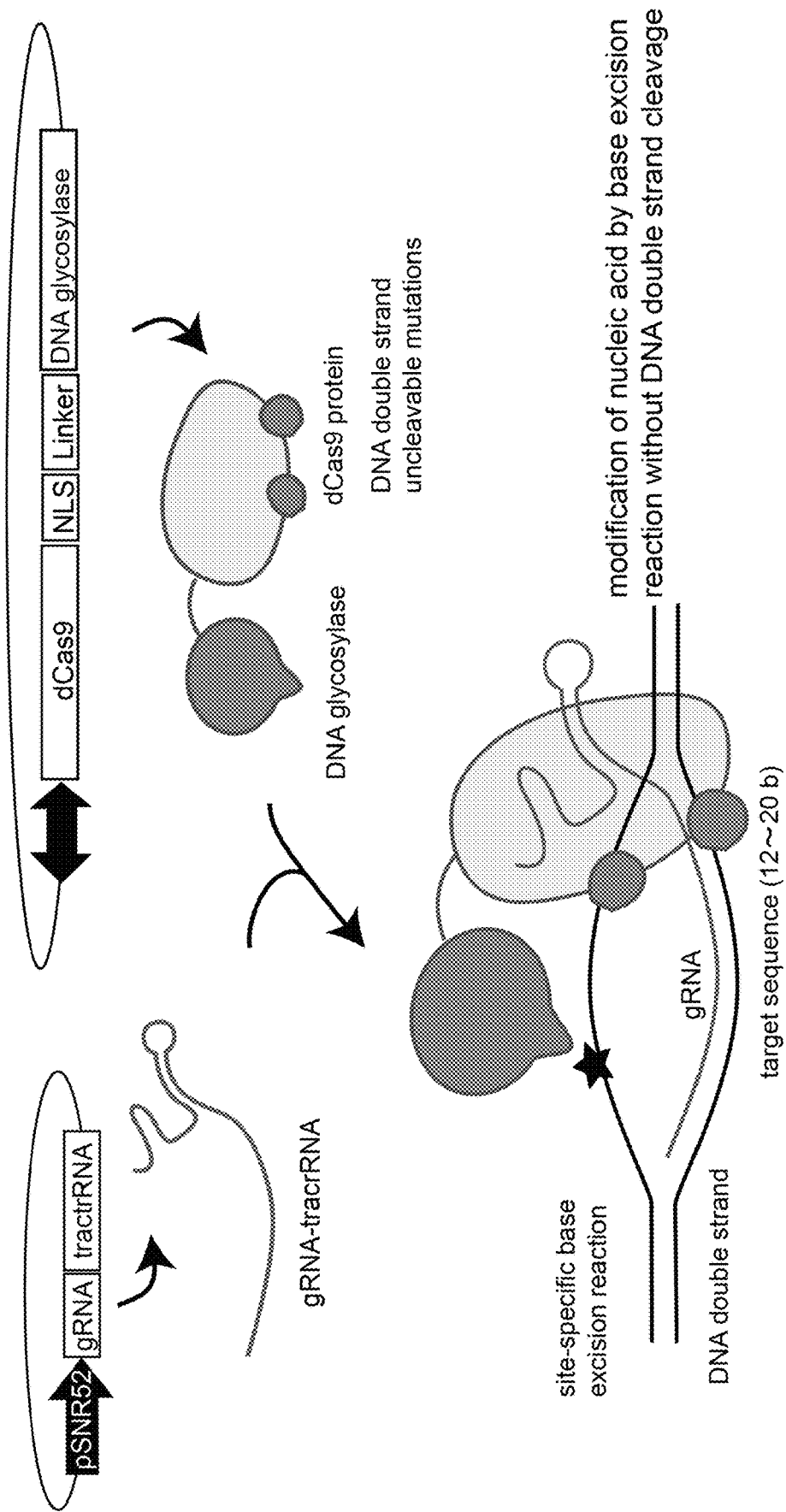
FIG. 2 is a schematic showing of a mechanism of the genetic modification method of the present invention using DNA glycosylase and the CRISPR-Cas system.

FIG. 2 is a schematic showing of the double stranded DNA modification method of the present invention using CRISPR-mutant Cas as a nucleic acid sequence-recognizing module.

The nucleic acid sequence-recognizing module of the present invention using CRISPR-mutant Cas is provided as a complex of an RNA molecule consisting of a guide RNA complementary to the target nucleotide sequence and tracrRNA necessary for recruiting mutant Cas protein, and a mutant Cas protein.

The Cas protein to be used in the present invention is not particularly limited as long as it belongs to the CRISPR system, and preferred is Cas9. Examples of Cas9 include, but are not limited to, *Streptococcus pyogenes*-derived Cas9 (SpCas9), *Streptococcus thermophilus*-derived Cas9 (StCas9) and the like. Preferred is SpCas9. AS a mutant Cas to be used in the present invention, any of Cas wherein the cleavage ability of the both strands of the double stranded DNA is inactivated and one having nickase activity wherein at least one cleavage ability of one strand alone is inactivated can be used. For example, in the case of SpCas9, a D10A mutant in which the 10th Asp residue is converted to an Ala residue and lacking cleavage ability of a strand opposite to the strand forming a complementary strand with a guide RNA, or H840A mutant in which the 840th His residue is converted to an Ala residue and lacking cleavage ability of strand complementary to guide RNA, or a double mutant thereof can be used, and other mutant Cas can be used similarly.

DNA glycosylase is provided as a complex with mutant Cas by a method similar to the coupling scheme with the above-mentioned zinc finger and the like. Alternatively, a DNA glycosylase and mutant Cas can also be bound by utilizing RNA aptamers MS2F6, PP7 and the like and RNA scaffold by binding proteins thereto. Guide RNA forms a complementary strand with the target nucleotide sequence, mutant Cas is recruited by the tracrRNA attached and mutant Cas recognizes DNA cleavage site recognition sequence PAM (protospacer adjacent motif) (when SpCas9 is used, PAM is 3 bases of NGG (N is any base), and, theoretically, can target any position on the genome). One or both DNAs cannot be cleaved, and, due to the action of the DNA glycosylase linked to the mutant Cas, base excision occurs in the targeted site (appropriately adjusted within several hundred bases including whole or partial target nucleotide sequence) and a AP site occurs in the double stranded DNA. Various mutations are introduced due to the errors made by the BER system of the cell to be repaired (see, for example, FIG. 5).

Even when CRISPR-mutant Cas is used as a nucleic acid sequence-recognizing module, a nucleic acid sequence-recognizing module and a DNA glycosylase are desirably introduced, in the form of a nucleic acid encoding same, into a cell having a double stranded DNA of interest, similar to when zinc finger and the like are used as a nucleic acid sequence-recognizing module.

A DNA encoding Cas can be cloned by a method similar to the above-mentioned method for a DNA encoding a DNA glycosylase, from a cell producing the enzyme. A mutant Cas can be obtained by introducing a mutation to convert an amino acid residue of the part important for the DNA cleavage activity (e.g., 10th Asp residue and 840th His residue for Cas9, though not limited thereto) to other amino acid, into a DNA encoding cloned Cas, by a site specific mutation induction method known per se.

Alternatively, a DNA encoding mutant Cas can also be constructed as a DNA showing codon usage suitable for expression in a host cell to be used, by a method similar to those mentioned above for a DNA encoding a nucleic acid sequence-recognizing module and a DNA encoding a DNA glycosylase, and by a combination of chemical synthesis or PCR method or Gibson Assembly method. For example, CDS sequence and amino acid sequence optimized for the expression of SpCas9 in eukaryotic cells are shown in SEQ ID NOs: 3 and 4. In the sequence shown in SEQ ID NO: 3, when "A" is converted to "C" in base No. 29, a DNA encoding a D10A mutant can be obtained, and when "CA" is converted to "GC" in base No. 2518-2519, a DNA encoding an H840A mutant can be obtained.

A DNA encoding a mutant Cas and a DNA encoding a DNA glycosylase may be linked to allow for expression as a fusion protein, or designed to be separately expressed using a binding domain, intein and the like, and form a complex in a host cell via protein-protein interaction and protein ligation. Alternatively, a design may be employed in which a DNA encoding mutant Cas and a DNA encoding DNA glycosylase are each split into two fragments at suitable split site, either fragments are linked to each other directly or via a suitable linker to express a nucleic acid-modifying enzyme complex as two partial complexes, which are associated and refolded in the cell to reconstitute functional mutant Cas having a particular nucleic acid sequence recognition ability, and a functional DNA glycosylase having a base excision reaction catalyst activity is reconstituted when the mutant Cas is bonded to the target nucleotide sequence. For example, a DNA encoding the N-terminal side fragment and a DNA encoding the C-terminal side fragment of mutant Cas are respectively prepared by the PCR method by using suitable primers; a DNA encoding the N-terminal side fragment and a DNA encoding the C-terminal side fragment of DNA glycosylase are prepared in the same manner; for example, the DNAs encoding the N-terminal side fragments are linked to each other, and the DNAs encoding the C-terminal side fragments are linked to each other by a conventional method, whereby a DNA encoding two partial complexes can be produced. Alternatively, a DNA encoding the N-terminal side fragment of mutant Cas and a DNA encoding the C-terminal side fragment of DNA glycosylase are linked; and a DNA encoding the N-terminal side fragment of DNA glycosylase and a DNA encoding the C-terminal side fragment of mutant Cas are linked, whereby a DNA encoding two partial complexes can also be produced. Respective partial complexes may be linked to allow for expression as a fusion protein, or designed to be separately expressed using a binding domain, intein and the like, and foil a complex in a host cell via protein-protein interaction and protein ligation. Two partial complexes may be linked to be expressed as a fusion protein. The split site of the mutant Cas is not particularly limited as long as the two split fragments can be reconstituted such that they recognize and bind to the target nucleotide sequence, and it may be split at one site to provide N-terminal side fragment and C-terminal side fragment, or not less than 3 fragments obtained by splitting at two or more sites may be appropriately linked to give two fragments. The three-dimensional structures of various Cas proteins are known, and those of ordinary skill in the art can appropriately select the split site based on such information. For example, since the region consisting of the 94th to the 718th amino acids from the N terminus of SpCas9 is a domain (REC) involved in the recognition of the target nucleotide sequence and guide RNA, and the region consisting of the 1099th amino acid to the C-terminal amino acid is the domain (PI) involved in the interaction with PAM, the N-terminal side fragment and the C-terminal side fragment can be split at any site in REC domain or PI domain, preferably in a region free of a structure (e.g., between 204th and 205th amino step from the N-terminal (204 . . . 205), between 535th and 536th amino acids from the N-terminal (535 . . . 536) and the like) (see, for example, Nat Biotechnol. 33(2): 139-142 (2015)).

The obtained DNA encoding a mutant Cas and/or a DNA glycosylase can be inserted into the downstream of a promoter of an expression vector similar to the one mentioned above, according to the host.

On the other hand, a DNA encoding guide RNA and tracrRNA can be obtained by designing an oligoDNA sequence linking guide RNA sequence complementary to the target nucleotide sequence and known tracrRNA sequence (e.g., gttttagagctagaaatagcaagttaaaataaggcta-gtccgttatcaacttgaaaaagtggc accgagtcggtggtgctttt; SEQ ID NO: 5) and chemically synthesizing using a DNA/RNA synthesizer. While a DNA encoding guide RNA and tracrRNA can also be inserted into an expression vector similar to the one mentioned above, according to the host. As the promoter, pol III system promoter (e.g., SNR6, SNR52, SCR1, RPR1, U6, H1 promoter etc.) and terminator (e.g., $T_6$ sequence) are preferably used.

An RNA encoding mutant Cas and/or a DNA glycosylase can be prepared by, for example, transcription to mRNA in a vitro transcription system known per se by using a vector encoding the above-mentioned mutant Cas and/or DNA encoding a DNA glycosylase as a template.

Guide RNA-tracrRNA can be obtained by designing an oligoDNA sequence linking a sequence complementary to the target nucleotide sequence and known tracrRNA sequence and chemically synthesizing using a DNA/RNA synthesizer.

A DNA or RNA encoding mutant Cas and/or a DNA glycosylase, guide RNA-tracrRNA or a DNA encoding same can be introduced into a host cell by a method similar to the above, according to the host.

Since conventional artificial nuclease accompanies double stranded DNA breaks (DSB), inhibition of growth and cell death assumedly caused by disordered cleavage of chromosome (off-target cleavage) occur by targeting a sequence in the genome. The effect thereof is particularly fatal for many microorganisms and prokaryotes, and prevents applicability. In the present invention, mutation is introduced not by DNA cleavage but by a base excision reaction on the DNA base, and therefore, drastic reduction of toxicity can be realized.

The modification of the double stranded DNA in the present invention does not prevent occurrence of cleavage of the double stranded DNA in a site other than the targeted site (appropriately adjusted within several hundred bases including whole or partial target nucleotide sequence). However, one of the greatest advantages of the present invention is avoidance of toxicity by off-target cleavage, which is generally applicable to any species. In preferable one embodiment, therefore, the modification of the double stranded DNA in the present invention does not accompany cleavage of DNA strand not only in a targeted site of a given double stranded DNA but in a site other than same.

As shown in the below-mentioned Examples, when sequence-recognizing modules are produced corresponding to the adjacent multiple target nucleotide sequences, and simultaneously used, the mutation introduction can be efficiency increased than by using a single nucleotide sequence as a target. As the effect thereof, similarly mutation induction is realized even when both target nucleotide sequences partly overlap or when the both are apart by about 600 bp. It can occur both when the target nucleotide sequences are in the same direction (target nucleotide sequences are present on the same strand), and when they are opposed (target nucleotide sequence is present on each strand of double stranded DNA).

The genome sequence modification method of the present invention can introduce mutation into almost all cells in which the nucleic acid-modifying enzyme complex of the present invention has been expressed, by selecting a suitable target nucleotide sequence. Thus, insertion and selection of a selection marker gene, which are essential in the conventional genome editing, are not necessary. This dramatically facilitates and simplifies gene manipulation and enlarges the applicability to crop breeding and the like since a recombinant organism with foreign DNA is not produced.

Since the genome sequence modification method of the present invention shows extremely high efficiency of mutation induction, and does not require selection by markers, modification of multiple DNA regions at completely different positions as targets can be performed. Therefore, in one preferable embodiment of the present invention, two or more kinds of nucleic acid sequence-recognizing modules that specifically bind to different target nucleotide sequences (which may be present in one object gene, or two or more different object genes, which object genes may be present on the same chromosome or different chromosomes) can be used. In this case, each one of these nucleic acid sequence-recognizing modules and DNA glycosylase form a nucleic acid-modifying enzyme complex. Here, a common DNA glycosylase can be used. For example, when CRISPR-Cas system is used as a nucleic acid sequence-recognizing module, a common complex of a Cas protein and a DNA glycosylase (including fusion protein) is used, and two or more kinds of chimeric RNAs of tracrRNA and each of two or more guide RNAs that respectively form a complementary strand with a different target nucleotide sequence are produced and used as guide RNA-tracrRNAs. On the other hand, when zinc finger motif, TAL effector and the like are used as nucleic acid sequence-recognizing modules, for example, a DNA glycosylase can be fused with a nucleic acid sequence-recognizing module that specifically binds to a different target nucleotide.

To express the nucleic acid-modifying enzyme complex of the present invention in a host cell, as mentioned above, an expression vector containing a DNA encoding the nucleic acid-modifying enzyme complex, or an RNA encoding the nucleic acid-modifying enzyme complex is introduced into a host cell. For efficient introduction of mutation, it is desirable to maintain an expression of nucleic acid-modifying enzyme complex of a given level or above for not less than a given period. From such aspect, it is ensuring to introduce an expression vector (plasmid etc.) autonomously replicatable in a host cell. However, since the plasmid etc. are foreign DNAs, they are preferably removed rapidly after successful introduction of mutation. When mutant AP endonuclease is used in combination, since the mutant enzyme inhibits the BER mechanism in the host cell, it may induce undesirable spontaneous mutations outside the target region. Thus, it is preferable to also remove a plasmid containing a DNA encoding the mutant enzyme promptly after introduction of the desired mutation. Therefore, though subject to change depending on the kind of host cell and the like, for example, the introduced plasmid is desirably removed from the host cell after a lapse of for 6 hr-2 days from the introduction of an expression vector by using various plasmid removal methods well known in the art.

Alternatively, as long as expression of a nucleic acid-modifying enzyme complex, which is sufficient for the introduction of mutation, is obtained, it is preferable to introduce mutation into the object double stranded DNA by transient expression by using an expression vector without autonomous replicatability in a host cell (e.g., vector etc. lacking replication origin that functions in host cell and/or gene encoding protein necessary for replication) or RNA.

The present invention is explained in the following by referring to Examples, which are not to be construed as limitative.

EXAMPLES

In the below-mentioned Examples, experiments were performed as follows.

<Cell Line, Culture, Transformation, and Expression Induction>

Budding yeast Saccharomyces cerevisiae BY4741 strain (requiring leucine and uracil) was cultured in a standard YPDA medium or SD medium with a Dropout composition meeting the auxotrophicity. The culture performed was stand culture in an agar plate or shaking culture in a liquid medium between 25° C. and 30° C. Transformation was performed by an acetic acid lithium method, and selection was made in SD medium meeting appropriate auxotrophicity. For expression induction by galactose, after preculture overnight in an appropriate SD medium, culture in SR medium with carbon source changed from 2% glucose to 2% raffinose overnight, and further culture in SGal medium with carbon source changed to 0.2% galactose for 3 hr to 20 about two nights were conducted for expression induction.

For the measurement of the number of surviving cells and Can1 mutation rate, a cell suspension was appropriately diluted, applied on SD plate medium or SD-Arg+60 mg/l Canavanine plate medium or SD+300 mg/l Canavanine plate medium, applied, and the number of colonies that emerge 3 days later was counted as the number of surviving cells. Using number of surviving colonies in SD plate as the total number of cells, and the number of surviving colonies in Canavanine plate as resistant mutant strain number, the mutation rate was calculated and evaluated. The site of mutation introduction was identified by amplifying DNA fragments containing the target gene region of each strain by a colony PCR method, performing DNA sequencing, and performing an alignment analysis based on the sequence of Saccharomyces Genome Database (www.yeastgenome.org/).

<Nucleic Acid Operation>

DNA was processed or constructed by any of PCR method, restriction enzyme treatment, ligation, Gibson Assembly method, and artificial chemical synthesis. For plasmid, as a yeast Escherichia coli shuttle vector, pRS315 for leucine selection and pRS426 for uracil selection were used as the backbone. Plasmid was amplified by Escherichia coli line XL-10 gold or DH5a, and introduced into yeast by the acetic acid lithium method.

<Construct>

For inducible expression, budding yeast pGal1/10 (SEQ ID NO: 6) which is a bidirectional promoter induced by galactose was used. At the downstream of the promoter, a nuclear localization signal (ccc aag aag aag agg aag gtg; SEQ ID NO: 7 (PKKKRV; encoding SEQ ID NO: 8)) was added to Streptococcus pyogenes-derived Cas9 gene ORF having a codon optimized for eucaryon expression (SEQ ID NO: 3) and the sequence of ORF (ORF of wild-type gene is shown in SEQ ID NO: 1, Y164A mutation is substitution of base number 490-491 ta with gc (ta490gc); Y164G mutation is substitution of base number 490-491 ta with gg (ta490gg); N222D mutation is substitution of base number 664 a with g (a664g); L304A mutation is substitution of base number 910-911 tt with gc (tt910gc); R308E mutation is substitution of base number 922-923 ag with ga (ag922ga); R308O mutation is substitution of base number 922-924 aga with tgt (aga922tgt)) of wild-type or various mutant uracil-DNA glycosylase genes (UNG1 derived from yeast Saccharomyces cerevisiae), excluding a region (base number 1-60) encoding the mitochondria localization signal, was ligated via a linker sequence and expressed as a fusion protein. For comparison, UNG1 gene instead of deaminase gene (PmCDA1 derived from Petromyzon marinus Petromyzon marinus) was ligated and expressed as a fusion protein. As a linker sequence, 2×GS linker (two repeats of ggt gga gga ggt tct; SEQ ID NO: 9 (GGGGS; encoding SEQ ID NO: 10)) was used. As a terminator, budding yeast-derived ADH1 terminator (SEQ ID NO: 11) and Top2 terminator (SEQ ID NO: 12) were ligated. In the domain integration method, Cas9 gene ORF was ligated to SH3 domain (SEQ ID NOs: 13 and 14) via 2×GS linker to give one protein, mutant yeast UNG1 added with SH3 ligand sequence (SEQ ID NOs: 15 and 16) as another protein and they were ligated to Gal1/10 promoter on both directions and simultaneously expressed. These were incorporated into pRS315 plasmid.

In Cas9, mutation to convert the 10th aspartic acid to alanine (D10A, corresponding DNA sequence mutation a29c) and mutation to convert the 840th histidine to alanine (H840A, corresponding DNA sequence mutation ca2518gc) were introduced to remove cleavage ability of each side of DNA strand.

gRNA as a chimeric structure with tracrRNA (derived from Streptococcus pyogenes; SEQ ID NO: 5) was disposed between SNR52 promoter (SEQ ID NO: 17) and Sup4 terminator (SEQ ID NO: 18), and incorporated into pRS426 plasmid. As gRNA target base sequence, 793-812 (aacccaggtgcctggggtcc; SEQ ID NO: 19) and 767-786 complementary strand sequence (ataacggaatccaactgggc; SEQ ID NO: 20) of CAN1 gene ORF were used. For simultaneous expression of multiple targets, a sequence from a promoter to a terminator as one set and a plurality thereof were incorporated into the same plasmid. They were introduced into cells along with Cas9-UNG1 expression plasmid, intracellularly expressed, and a complex of gRNA-tracrRNA and Cas9-UNG1 was formed.

Example 1: Modification of Genome Sequence by Linking DNA Sequence Recognition Ability of CRISPR-Cas to Mutant Uracil-DNA Glycosylase (1)

Figure 3:
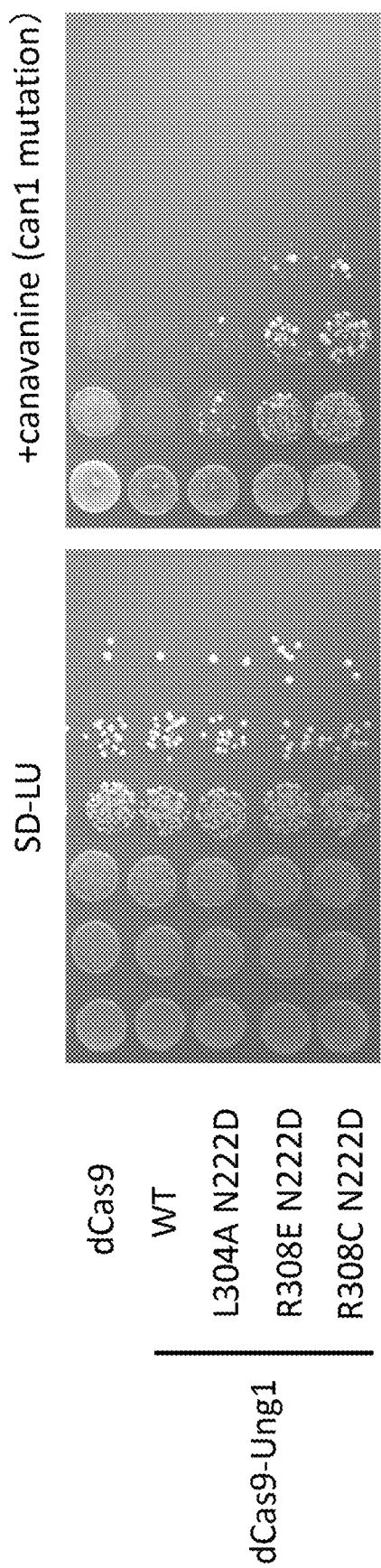
FIG. 3 shows the results of verification, by using a budding yeast, of the effect of the genetic modification method of the present invention comprising a CRISPR-Cas system and mutant uracil-DNA glycosylase derived from budding yeast (having CDG activity and decreased reactivity with DNA having unrelaxed double helix structure) in combination.

To test the effect of genome sequence modification technique of the present invention by utilizing mutant uracil-DNA glycosylase and CRISPR-Cas nucleic acid sequence recognition ability, introduction of mutation into CAN1 gene encoding canavanine transporter that acquire canavanine-resistance due to gene deficiency was tried. As gRNA, a sequence complementary to 793-812 of CAN1 gene ORF and a sequence complementary to 767-786 complementary strand sequence were used, a chimeric RNA expression vector obtained by linking thereto Streptococcus pyogenes-derived tracrRNA, and a vector expressing a protein obtained by fusing dCas9 with impaired nuclease activity by introducing mutations (D10A and H840A) into *Streptococcus pyogenes*-derived Cas9 (SpCas9), and wild-type yeast-derived UNG1 or yeast-derived UNG1 introduced with various mutations (N222D single mutation and double mutation of N222D and L304A, R308E or R308C mutation) were constructed, introduced into the budding yeast by the acetic acid lithium method, and coexpressed. The results are shown in FIG. 3. When cultured on a canavanine-containing SD plate, only the cells subjected to introduction and expression of gRNA-tracrRNA and dCas9-mutant UNG1 (double mutant of N222D mutation imparting CDG activity and L304A, R308E or R3080 mutation that decreases reactivity with DNA having an unrelaxed double helix structure) formed canavanine-resistant colonies. With N222D single mutation, the cytotoxicity was strong, and cell culture and evaluation were difficult, and therefore, the results are not shown. From the above, it was shown that target specific mutation introduction becomes possible by decreasing the reactivity of DNA glycosylase with a DNA having an unrelaxed double helix structure.

Example 2: Modification of Genome Sequence by Linking DNA Sequence Recognition Ability of CRISPR-Cas to Mutant Uracil-DNA Glycosylase (2)

Figure 4:
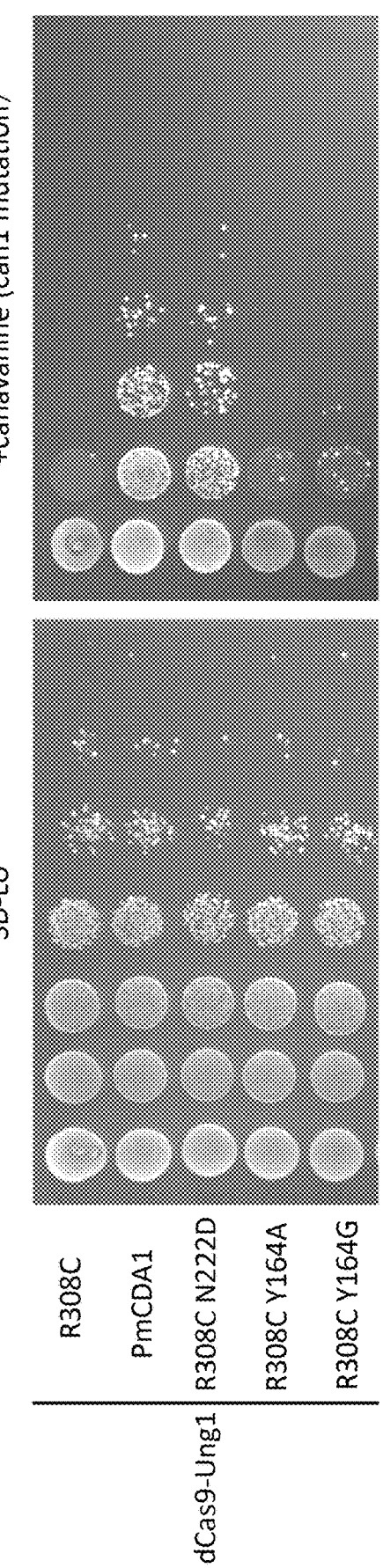
FIG. 4 shows the results of verification, by using a budding yeast, of the effect of the genetic modification method of the present invention comprising a CRISPR-Cas system and budding yeast-derived mutant uracil-DNA glycosylase (having CDG activity or TDG activity and decreased reactivity with DNA having unrelaxed double helix structure) in combination.

Using yeast UNG1 introduced with double mutation of R308C mutation that decreases reactivity with a DNA having an unrelaxed double helix structure, and N222D mutation imparting CDG activity, or Y164A or Y164G mutation imparting TDG activity, and by a method similar to that in Example 1, introduction of mutation into CAN1 gene was tried. The results are shown in FIG. 4. It was shown that R3080 N222D can achieve efficiency of mutation induction comparable to that of deaminase PmCDA1, and mutant strain can be obtained even without selection. It was shown that thymine base could be edited, since canavanine-resistant colony was also obtained in R3080 Y164A. Y164G mutation improved the efficiency of mutation induction.

Figure 5:
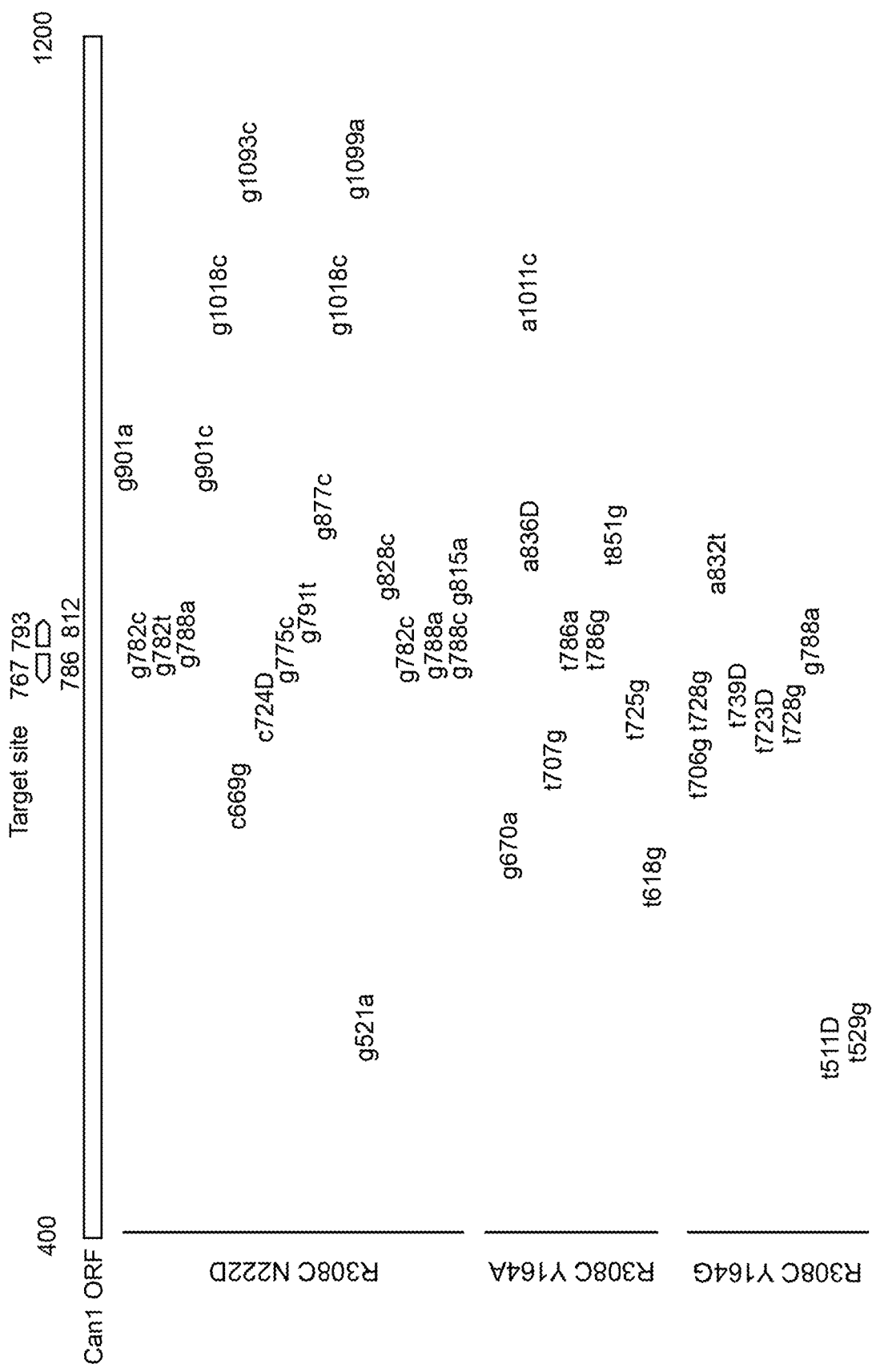
FIG. 5 shows the analysis results of mutated sites in the canavanine-resistant colony obtained in FIG. 4.

Then, each canavanine-resistant clone was subjected to the sequence analysis of the Can1 gene region. The results are shown in FIG. 5. Mutations were somewhat randomly centered around two adjacent target sites (767-786, 793-812). This is different from the pinpoint introduction of mutation by deaminase (WO 2015-133554), and suggests that the genome editing technique of the present invention is suitable for random introduction of mutation into the target nucleotide sequence and in the vicinity thereof. As assumed, point mutation from C or G was mainly found in N222D, and point mutation from T or A was mainly found in Y164A and Y164G.

Example 3: Use of Different Coupling Scheme

Figure 6:
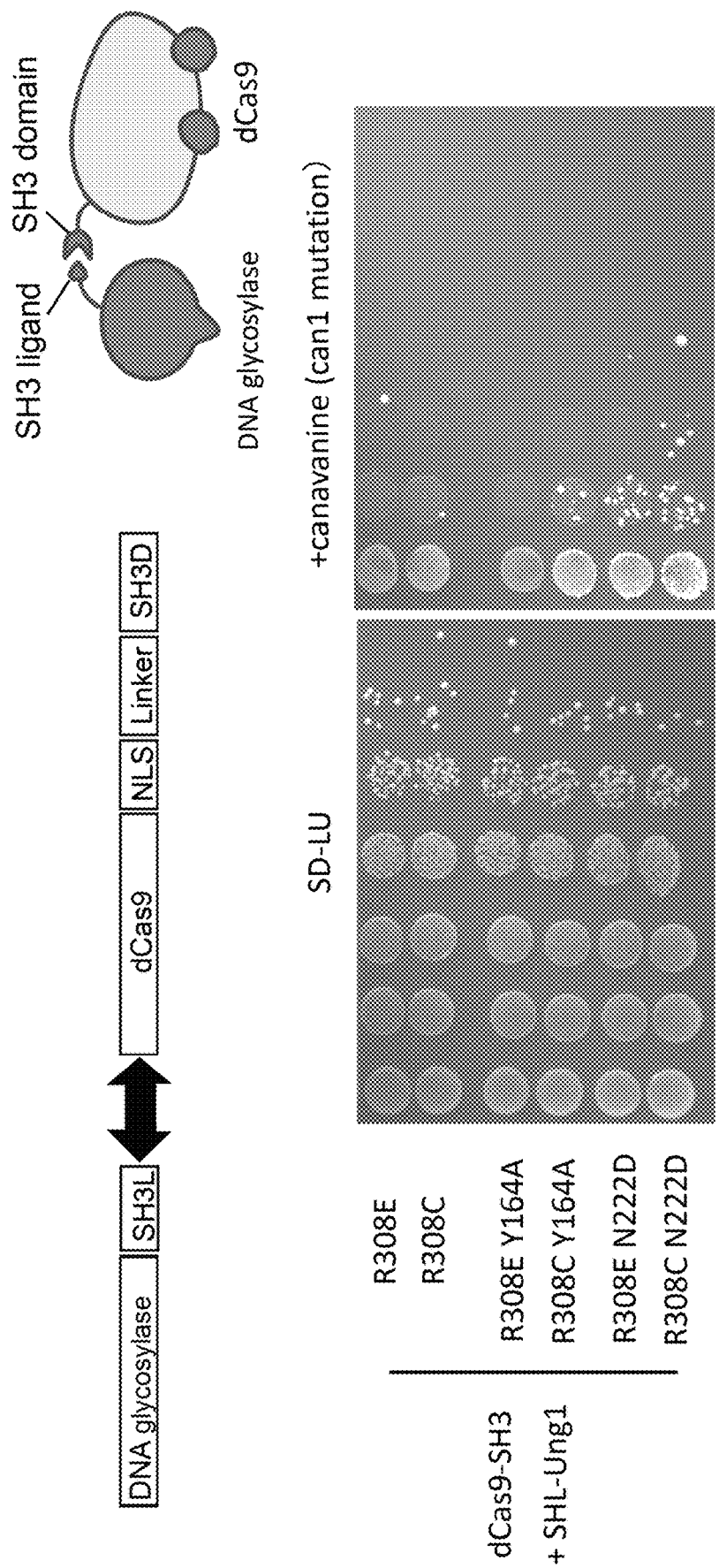
FIG. 6 shows the results when an expression construct constructed such that budding yeast-derived mutant uracil-DNA glycosylase and dCas9 are bound via SH3 domain and a binding ligand thereof is introduced into a budding yeast together with two kinds of gRNA.

Whether mutation can be introduced into a targeted gene even when Cas9 and DNA glycosylase are not used as a fusion protein but when a nucleic acid-modifying enzyme complex is formed via a binding domain and a ligand thereof was examined. As Cas9, dCas9 used in Example 1 was used, yeast UNG1 mutant (double mutant of N222D or Y164A mutation, and R308E or R308C mutant) was used as DNA glycosylase, SH3 domain was fused with the former, and a binding ligand thereof was fused with the latter to produce various constructs shown in FIG. 6. In the same manner as in Example 1, sequences in the CAN1 gene were used as gRNA targets, and these constructs were introduced into a budding yeast. As a result, even when dCas9 and DNA glycosylase were bound via the binding domain, mutation was efficiently introduced into the targeted site of the CAN1 gene (FIG. 6).

Figure 7:
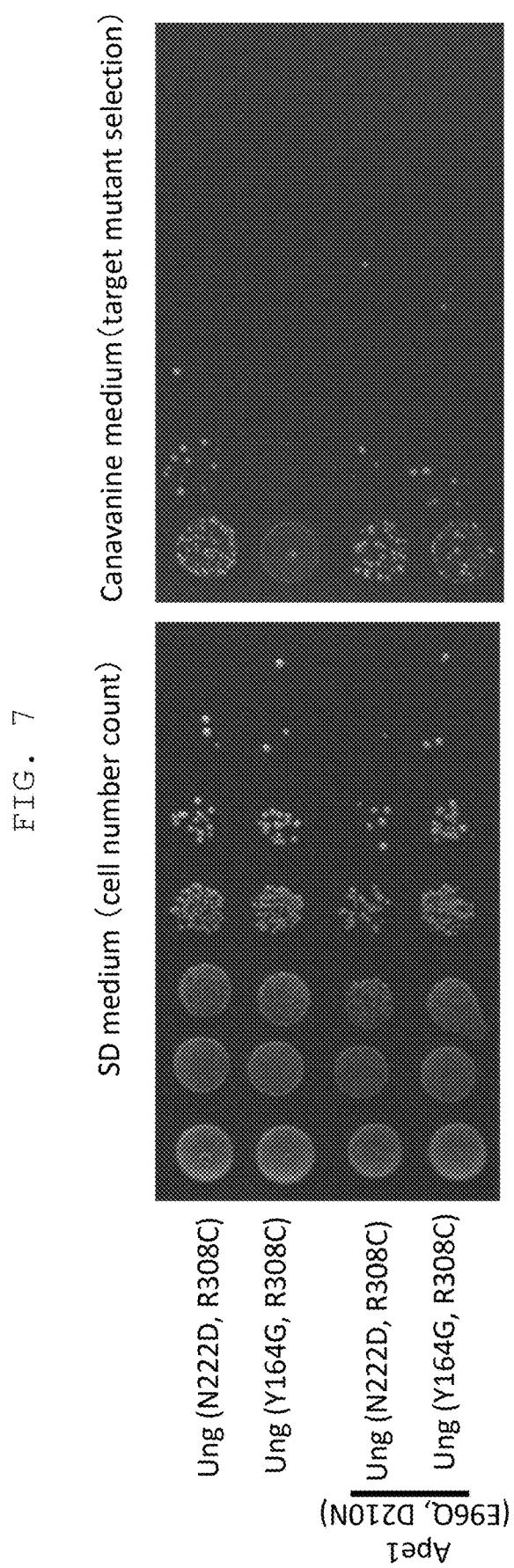
FIG. 7 shows that the efficiency of mutation induction by mutant UNG1 ("Ung" in Figure means UNG1 derived from yeast, hereinafter the same) is improved by coexpression of AP endonuclease (Ape1) mutants (E96Q, D210N).

Example 4 Improvement of Efficiency of Mutation Induction by Coexpression of Mutant AP Endonuclease Using yeast UNG1 introduced with double mutation of R308C mutation that decreases reactivity with a DNA having an unrelaxed double helix structure, and N222D mutation imparting CDG activity or Y164G mutation imparting TDG activity, and mutant human APE1 (E96Q, D210N) which lost enzyme activity but retained binding capacity to AP site, and by a method similar to that in Example 1, introduction of mutation into CAN1 gene was tried. The results are shown in FIG. 7. When mutant APE1 was coexpressed, the number of canavanine-resistant colonies increased even in Y164G, R3080 that showed low efficiency when used alone, and efficiency of mutation introduction targeting thymine was remarkably improved.

Figure 8:
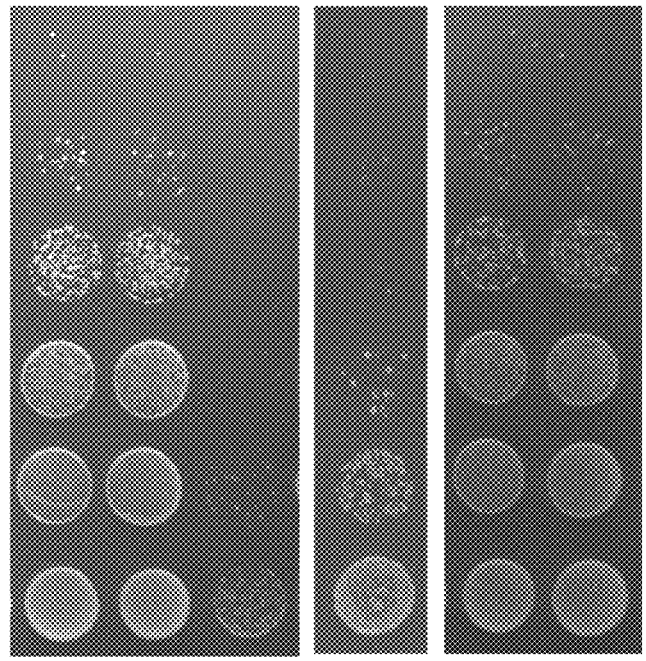
FIG. 8 shows that cytotoxicity in a host yeast introduced with mutant UNG1 having CDG activity (N222D) or TDG activity (Y164A) can be avoided by introducing a mutation (L304A) that decreases reactivity with a DNA having an unrelaxed double helix structure.

Example 5 Reduction of Cytotoxicity by Introduction of Mutation that Decreases Reactivity with DNa Having an Unrelaxed Double Helix Structure An influence of the presence or absence of mutation (L304A) that decreases reactivity with a DNA having an unrelaxed double helix structure in UNG1 on the survival rate of the host yeast was examined. The results are shown in FIG. 8. The host yeast introduced with mutant UNG1 having only the mutation imparting CDG activity (N222D) or TDG activity (Y164A) showed a marked decrease in the survival rate as compared to the yeast introduced with wild-type UNG1. This is assumed to be because wild-type UNG1 removes uracil which is an aberrant base that appears rarely in DNA, whereas mutant UNG1 having CDG activity or TDG activity removes cytosine or thymine anywhere on the genomic DNA and produces mutations undesirable for the survival of the cell. On the other hand, when the reactivity with a DNA having an unrelaxed double helix structure is decreased by introducing L304 mutation, the survival rate of the host yeast recovered remarkably and cytotoxicity could be avoided.

Example 6 Utilization of Heterogenous Uracil-DNA Glycosylase

Figure 9:
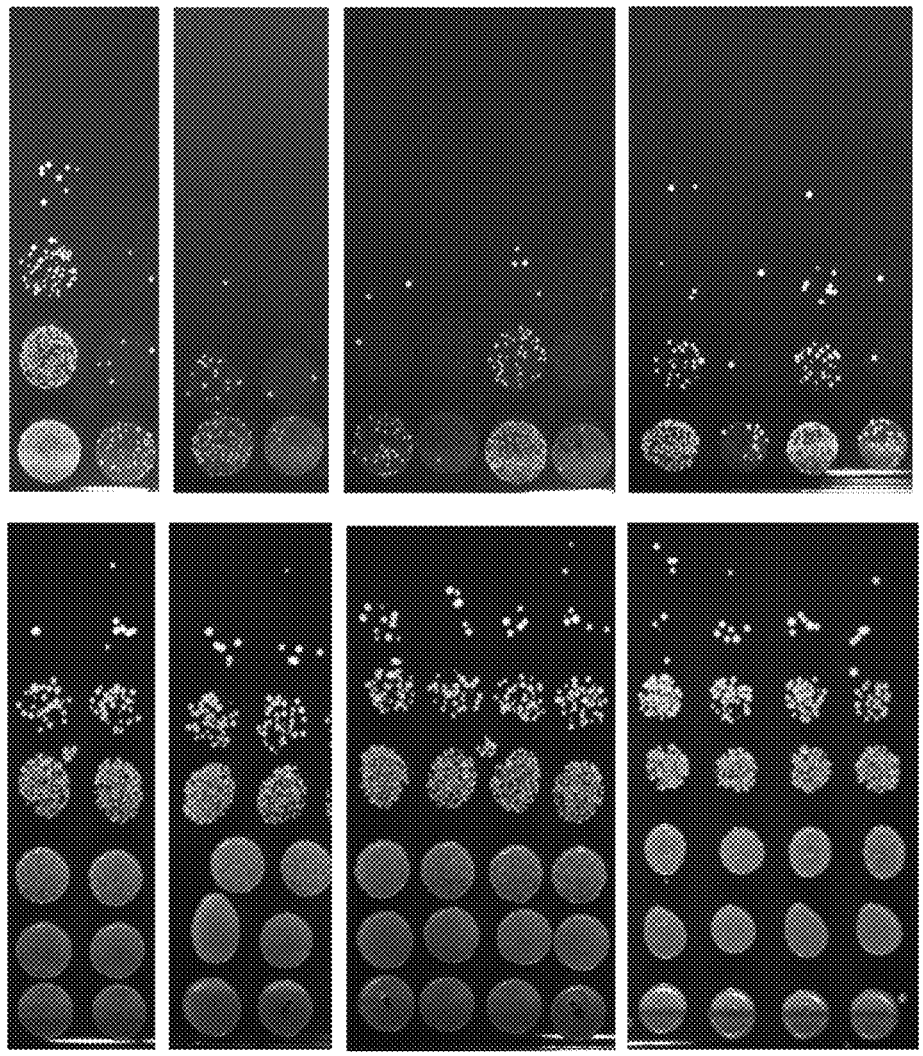
FIG. 9 shows survival rate and efficiency of mutation induction in a yeast introduced with a heterogenous mutant uracil-DNA glycosylase derived from *Escherichia coli* or vaccinia virus (EcUDG or vvUDG). vvUDG did not cause cytotoxicity in a host yeast even without introduction of a mutation (R187C) that decreases reactivity with a DNA having an unrelaxed double helix structure. The efficiency of mutation induction by vvUDG was remarkably improved by coexpression of A20 protein.
Figure 10:
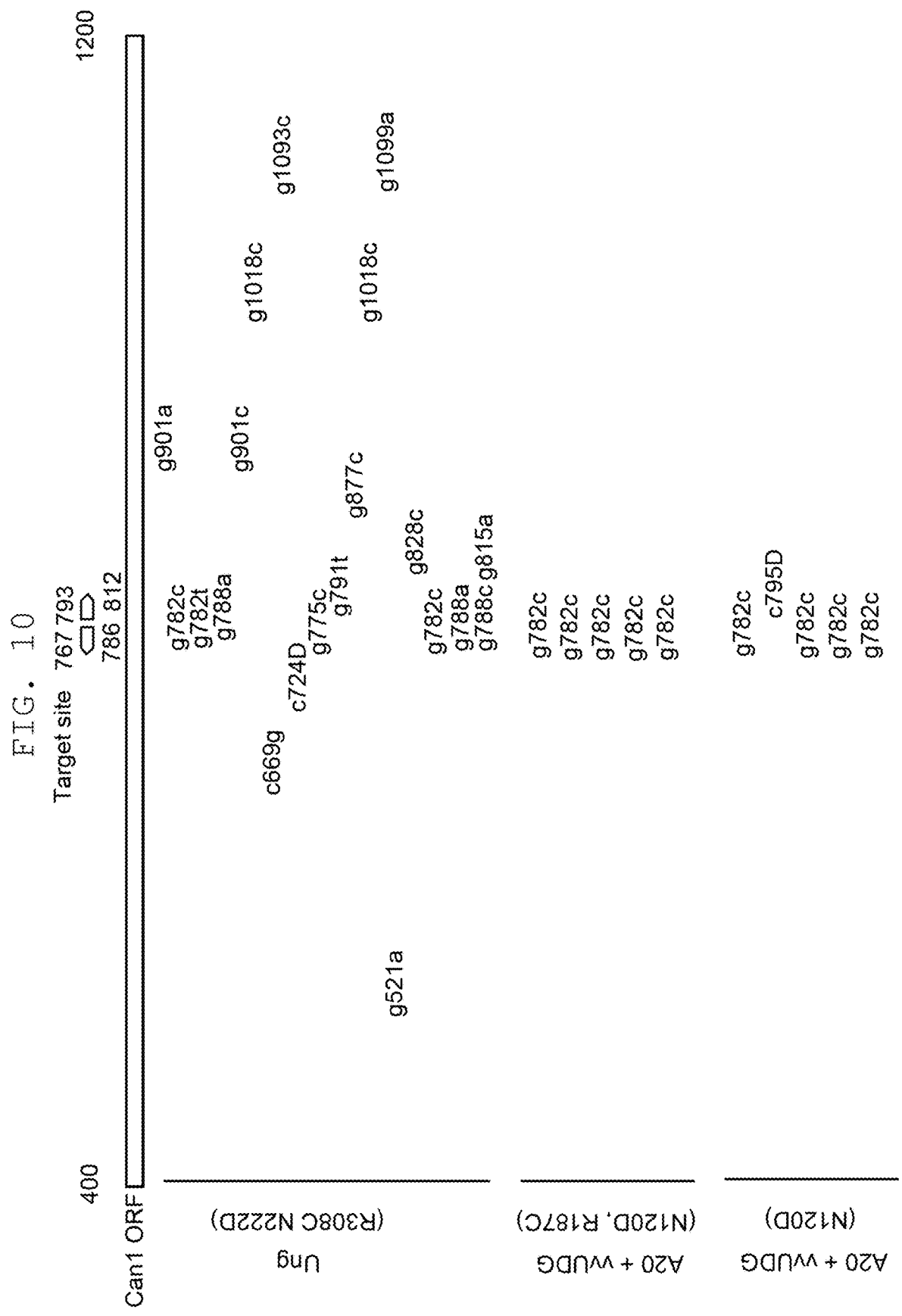
FIG. 10 shows comparison of mutation introduction sites between mutant UNG1 derived from yeast and mutant UDG derived from vaccinia virus (vvUDG) in the target nucleotide sequences and in the vicinity thereof.

Whether introduction of targeted mutation into the host yeast is possible even when heterogenous mutant UNG1 is used instead of mutant UNG1 derived from yeast was examined. Two kinds of *Escherichia coli*-derived mutant ungs (EcUDG) (N123D/L191A double mutant, Y66G/L191A double mutant) and four kinds of vaccinia virus-derived mutant UDGs (vvUDG) (N120D/R187C double mutant, Y70G/R187C double mutant, N120D mutant, Y70G mutant) were used. The results are shown in FIG. 9. While both EcUDG, vvUDG were functional in yeast, the efficiency of mutation induction was low as compared to yeast UNG1, and it was shown that the use of allogeneic DNA glycosylase was advantageous. Surprisingly, it was clarified that cytotoxicity was absent in vvUDG, regardless of the presence or absence of R187C mutation corresponding to R3080 mutation of yeast UNG1. As a result of sequence analysis, since mutation by vvUDG was concentrated in a specific base in the target nucleotide sequence regardless of the presence or absence of R187C mutation (see FIG. 10), vvUDG was suggested to be a DNA glycosylase with natively sufficiently low reactivity with a DNA having an unrelaxed double helix structure. The efficiency of mutation induction by vvUDG was remarkably increased in virus DNA polymerase by coexpressing A20, which interacts with vvUDG and acts as a processivity factor (FIG. 9).

Example 7 Reduction of Non-Specific Mutation by Utilization of Split Enzyme

Figure 11:
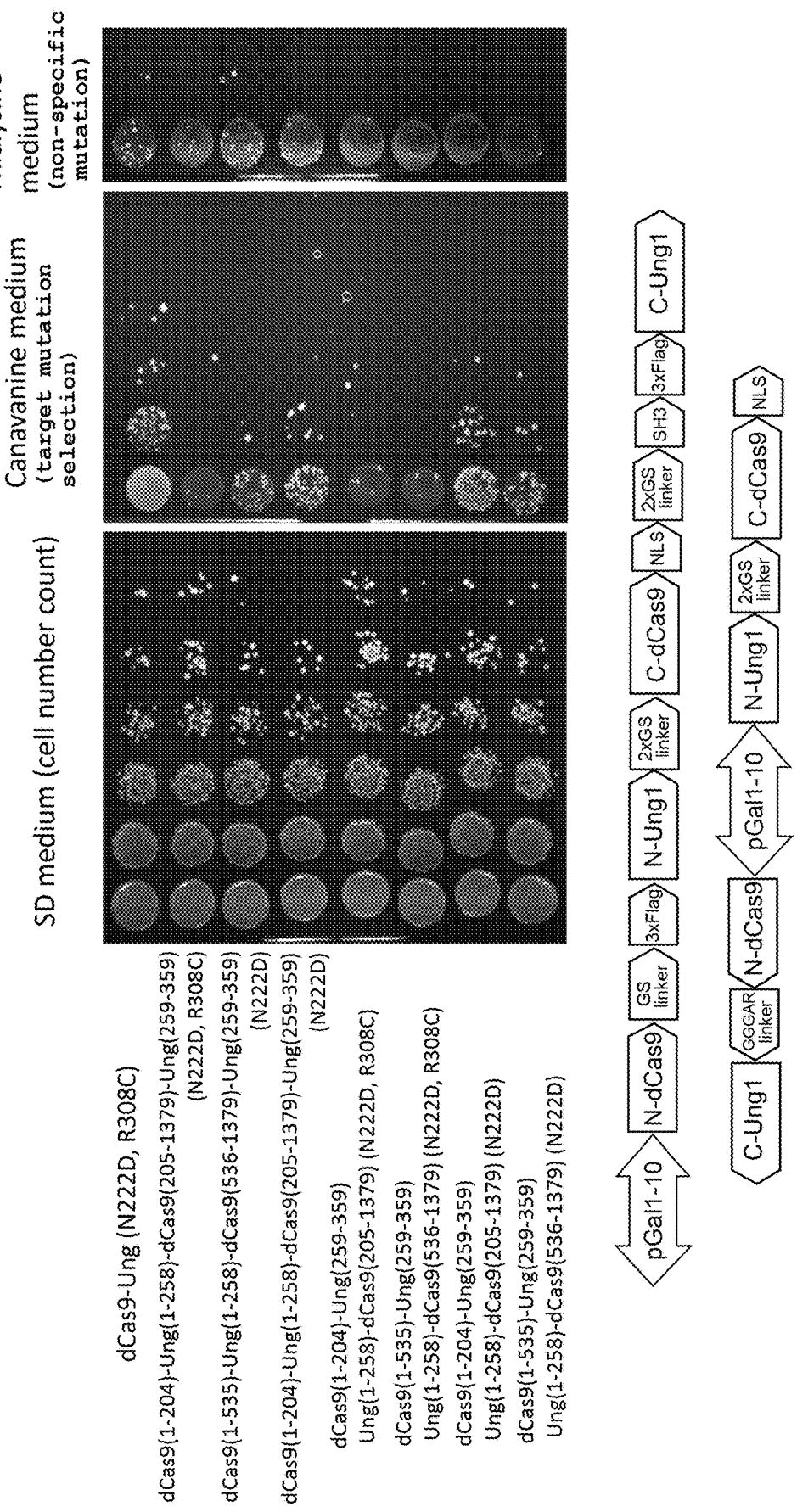
FIG. 11 shows that non-specific mutation by mutant UNG1 can be reduced by utilizing a split enzyme.

In addition to the utilization of mutation that decreases reactivity with a DNA having an unrelaxed double helix structure, and DNA glycosylase with natively low reactivity with a DNA having a double helix structure such as vvUDG, utilization of split enzyme technique was tried as a different means for reducing non-specific mutation by DNA glycosylase. The plasmids shown in FIG. 11 containing DNA encoding various split enzymes were introduced into the host yeast together with a plasmid containing a DNA encoding guide RNA-tracrRNA by a method similar to that in Example 1, and the cell number, the number of canavanine-resistant (mutation at targeted site) colonies, the number of thialysine-resistant (non-specific mutation) colonies on a nonselective medium were examined. The survival rate of the host yeast on a nonselective medium was equivalent to that when mutant UNG1 introduced with mutation (R3080) that decreases reactivity with a DNA having an unrelaxed double helix structure was introduced even when any split enzyme was used. Thus, it was shown that cytotoxicity can be sufficiently decreased by the utilization of a split enzyme, even without introducing a mutation that decreases reactivity with a DNA having an unrelaxed double helix structure, whereby it was suggested that non-specific mutation can be suppressed (FIG. 11). In fact, the frequency of non-specific mutation by using thialysine-resistance as an index was decreased by the utilization of a split enzyme (FIG. 11).

INDUSTRIAL APPLICABILITY

The present invention makes it possible to safely introduce site specific mutation into any species without accompanying insertion of a foreign DNA or double-stranded DNA breaks. It is also possible to set a wide range of mutation introduction to target nucleotide sequence and several hundred bases in the vicinity thereof, and the technique can also be applied to topical evolution induction by introduction of random mutation into a particular restricted region, which has been almost impossible heretofore, and is extremely useful. Furthermore, when mutation imparting CDG activity and mutation imparting TDG activity are imparted to UNG, base excision using 5-methylcytidine as a substrate becomes possible. According to the present invention, therefore, the epigenome information can be rewritten into, for example, region-specific release of methylation state to change the gene expression pattern and the like. Therefore, artificial cell differentiation, cancer cell inhibition, modification of gene function without rewriting genome sequence, and the like become possible.

This application is based on a patent application No. 2014-224745 filed in Japan (filing date: Nov. 4, 2014), the contents of which are incorporated in full herein.

The invention claimed is:

1. A method of modifying a targeted site of a double stranded DNA in a eukaryotic cell, comprising
contacting a complex with the double stranded DNA, wherein the complex comprises a nucleic acid sequence-recognizing module and a mutant of uracil DNA glycosylase having reduced reactivity with unrelaxed DNA to avoid cytotoxicity,
wherein the nucleic acid sequence-recognizing module specifically binds to a target nucleotide sequence in the targeted site of the double stranded DNA,
wherein the mutant of uracil DNA glycosylase is
(i-a) a mutant of yeast UNG1 having N222D/L304A mutations, N222D/R308E mutations, N222D/R308C mutations, Y164A/L304A mutations, Y164A/R308E mutations, Y164A/R308C mutations, Y164G/L304A mutations, Y164G/R308E mutations, Y164G/R308C mutations, N222D/Y164A/L304A mutations, N222D/Y164A/R308E mutations, N222D/Y164A/R308C mutations, N222D/Y164G/L304A mutations, N222D/Y164G/R308E mutations or N222D/Y164G/R308C mutations, or
(i-b) a mutant of Uracil DNA Glycosylase (UNG) other than a mutant of (i-a) and having mutations corresponding to the mutations of the mutant of (i-a),
thereby converting one or more nucleotides in the targeted site to other one or more nucleotides or deleting one or more nucleotides, or inserting one or more nucleotides into said targeted site, without a double stranded DNA break in the targeted site.

2. The method according to claim 1, wherein the nucleic acid sequence-recognizing module is selected from the group consisting of a clustered regularly interspaced short palindromic repeats (CRISPR)-associated (CRISPR-Cas) system wherein at least one DNA cleavage ability of Cas nuclease is inactivated, a zinc finger motif, a transcription activator-like effector and a pentatricopeptide repeat motif.

3. The method according to claim 1, wherein the nucleic acid sequence-recognizing module is a CRISPR-Cas system wherein at least one DNA cleavage ability of Cas nuclease is inactivated.

4. The method according to claim 3, wherein the Cas nuclease is Cas9 nuclease.

5. The method according to claim 1, wherein the double stranded DNA is further contacted with a factor that changes a DNA double stranded structure.

6. The method according to claim 1, which uses two or more kinds of nucleic acid sequence-recognizing modules each specifically binding to a different target nucleotide sequence.

7. The method according to claim 6, wherein the different target nucleotide sequences are present in different genes.

8. The method according to claim 1, further comprising contacting the double stranded DNA with a mutant of apurinic/apyrimidinic endonuclease having binding capacity to an abasic site but lacking nuclease activity.

9. The method according to claim 1, wherein the double stranded DNA is contacted with the complex by introducing a nucleic acid comprising a sequence encoding the nucleic acid sequence-recognizing module and a sequence encoding the mutant of uracil DNA glycosylase into a eukaryotic cell having the double stranded DNA.

10. The method according to claim 9, wherein the cell is a microbial cell.

11. The method according to claim 9, wherein the cell is a plant cell, an insect cell, or an animal cell.

12. The method according to claim 11, wherein the animal cell is a vertebrate cell.

13. The method according to claim 12, wherein the vertebrate cell is a mammalian cell.

14. The method according to claim 9, wherein the cell is a polyploid cell, and all of the targeted sites in alleles on a homologous chromosome are modified.

15. The method according to claim 1, wherein the mutant of UNG of (i-b) is a mutant of ung derived from *Escherichia coli*, mutant of UNG2 derived from yeast, or mutant of UNG1 or UNG2 derived from human, mouse, swine, bovine, horse or monkey.

16. The method according to claim 1, wherein the complex is formed via an interaction of a protein binding domain fused to the nucleic acid sequence-recognizing module and a binding partner of the domain fused to the mutant of uracil DNA glycosylase.

17. The method according to claim 1, wherein the mutant of uracil DNA glycosylase is (i-a) a mutant of yeast UNG1 having N222D/R308C mutations or N222D/Y164G/R308C mutations, or (i-b) a mutant of Uracil DNA Glycosylase (UNG) other than a mutant of (i-a) and having mutations corresponding to the mutations of the mutant of (i-a).

18. A method of modifying a targeted site of a double stranded DNA in a eukaryotic cell, comprising contacting a complex with the double stranded DNA, wherein the complex comprises a nucleic acid sequence-recognizing module and a mutant of uracil DNA glycosylase having reduced reactivity with unrelaxed DNA to avoid cytotoxicity, wherein the nucleic acid sequence-recognizing module specifically binds to a target nucleotide sequence in the targeted site of the double stranded DNA, wherein the mutant of uracil DNA glycosylase is (i-a) a mutant of yeast UNG1 having N222D/L304A mutations, N222D/R308E mutations, N222D/R308C mutations, Y164A/L304A mutations, Y164A/R308E mutations, Y164A/R308C mutations, Y164G/L304A mutations, Y164G/R308E mutations, Y164G/R308C mutations, N222D/Y164A/L304A mutations, N222D/Y164A/R308E mutations, N222D/Y164A/R308C mutations, N222D/Y164G/L304A mutations, N222D/Y164G/R308E mutations or N222D/Y164G/R308C mutations, or (i-b) or a mutant of Uracil DNA Glycosylase (UNG) other than a mutant of (i-a) and having mutations corresponding to the mutations of the mutant of (i-a), wherein the mutant of uracil DNA glycosylase, and an element of the nucleic acid sequence-recognizing module which is directly bonded to the mutant of uracil DNA glycosylase are respectively split into two fragments, the fragments of either of the mutant of uracil DNA glycosylase and the element are respectively linked to the fragments of the other to provide two partial complexes, and when the partial complexes are refolded with each other, the nucleic acid sequence-recognizing module is capable of specifically binding to the target nucleotide sequence and the specific bond enables the mutant of uracil DNA glycosylase to exhibit enzyme activity.

19. The method according to claim 18, wherein the element of the nucleic acid sequence-recognizing module which is directly bonded to the mutant of uracil DNA glycosylase is a mutant of Cas nuclease wherein at least one of the DNA cleavage abilities is inactivated.

20. The method according to claim 19, wherein the Cas nuclease is Cas9 nuclease.

21. The method according to claim 18, wherein the two partial complexes are provided as separate molecule complexes, and are refolded by association thereof in the cell.

22. The method according to claim 18, wherein the mutant of uracil DNA glycosylase is (i-a) a mutant of yeast UNG1 having N222D/R308C mutations or N222D/Y164G/R308C mutations, or (i-b) a mutant of Uracil DNA Glycosylase (UNG) other than a mutant of (i-a) and having mutations corresponding to the mutations of the mutant of (i-a).

23. A nucleic acid-modifying enzyme complex comprising (a) a nucleic acid sequence-recognizing module and (b) a mutant of uracil DNA glycosylase having reduced reactivity with unrelaxed DNA to avoid cytotoxicity, wherein the nucleic acid sequence-recognizing module specifically binds to a target nucleotide sequence in the targeted site of the double stranded DNA, wherein the mutant of uracil DNA glycosylase is (i-a) a mutant of yeast UNG1 having N222D/L304A mutations, N222D/R308E mutations, N222D/R308C mutations, Y164A/L304A mutations, Y164A/R308E mutations, Y164A/R308C mutations, Y164G/L304A mutations, Y164G/R308E mutations, Y164G/R308C mutations, N222D/Y164A/L304A mutations, N222D/Y164A/R308E mutations, N222D/Y164A/R308C mutations, N222D/Y164G/L304A mutations, N222D/Y164G/R308E mutations or N222D/Y164G/R308C mutations, or (i-b) a mutant of Uracil DNA Glycosylase (UNG) other than a mutant of (i-a) and having mutations corresponding to the mutations of the mutant of (i-a).

24. The complex according to claim 23, wherein the nucleic acid sequence-recognizing module is selected from the group consisting of a clustered regularly interspaced short palindromic repeats (CRISPR)-CRISPR associated system wherein at least one DNA cleavage ability of Cas nuclease is inactivated, a zinc finger motif, a transcription activator-like effector and a pentatricopeptide repeat motif.

25. The nucleic acid-modifying enzyme complex according to claim 23, wherein the mutant of uracil DNA glycosylase is (i-a) a mutant of yeast UNG1 having N222D/R308C mutations or N222D/Y164G/R308C mutations, or (i-b) a mutant of Uracil DNA Glycosylase (UNG) other than a mutant of (i-a) and having mutations corresponding to the mutations of the mutant of (i-a).

26. A nucleic acid comprising a sequence encoding a nucleic acid sequence-recognizing module, and a sequence encoding a mutant of uracil DNA glycosylase having reduced reactivity with unrelaxed DNA to avoid cytotoxicity, wherein the nucleic acid sequence-recognizing module specifically binds to a target nucleotide sequence in the targeted site of the double stranded DNA, wherein the mutant of uracil DNA glycosylase is (i-a) a mutant of yeast UNG1 having N222D/L304A mutations, N222D/R308E mutations, N222D/R308C mutations, Y164A/L304A mutations, Y164A/R308E mutations, Y164A/R308C mutations, Y164G/L304A mutations, Y164G/R308E mutations, Y164G/R308C mutations, N222D/Y164A/L304A mutations, N222D/Y164A/R308E mutations, N222D/Y164A/R308C mutations, N222D/Y164G/L304A mutations, N222D/Y164G/R308E mutations or N222D/Y164G/R308C mutations, or (i-b) a mutant of Uracil DNA Glycosylase (UNG) other than a mutant of (i-a) and having mutations corresponding to the mutations of the mutant of (i-a).

27. The nucleic acid according to claim 26, wherein the nucleic acid sequence-recognizing module is selected from the group consisting of a clustered regularly interspaced short palindromic repeats (CRISPR)-CRISPR associated system wherein at least one DNA cleavage ability of Cas nuclease is inactivated, a zinc finger motif, a transcription activator-like effector and a pentatricopeptide repeat motif.

28. The nucleic acid according to claim 26, wherein the mutant of uracil DNA glycosylase is (i-a) a mutant of yeast UNG1 having N222D/R308C mutations or N222D/Y164G/R308C mutations, or (i-b) a mutant of Uracil DNA Glycosylase (UNG) other than a mutant of (i-a) and having mutations corresponding to the mutations of the mutant of (i-a).

* * * * *